(12) United States Patent
Ghosh

(10) Patent No.: US 9,656,087 B2
(45) Date of Patent: May 23, 2017

(54) DELIVERY OF BI-VENTRICULAR PACING THERAPY IN A CARDIAC MEDICAL DEVICE AND MEDICAL DEVICE SYSTEM

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 14/919,912

(22) Filed: Oct. 22, 2015

(65) Prior Publication Data

US 2017/0028203 A1    Feb. 2, 2017

Related U.S. Application Data

(60) Provisional application No. 62/199,409, filed on Jul. 31, 2015, provisional application No. 62/199,424, filed on Jul. 31, 2015.

(51) Int. Cl.
| | |
|---|---|
| *A61N 1/00* | (2006.01) |
| *A61N 1/368* | (2006.01) |
| *A61N 1/05* | (2006.01) |
| *A61N 1/375* | (2006.01) |
| *A61N 1/39* | (2006.01) |

(52) U.S. Cl.
CPC .......... *A61N 1/3684* (2013.01); *A61N 1/056* (2013.01); *A61N 1/3682* (2013.01); *A61N 1/3756* (2013.01); *A61N 1/3956* (2013.01)

(58) Field of Classification Search
CPC ... A61N 1/3756; A61N 1/3684; A61N 1/3682
See application file for complete search history.

(56) References Cited

U.S. PATENT DOCUMENTS

| | | |
|---|---|---|
| 5,193,550 A | 3/1993 | Duffin |
| 5,354,316 A | 10/1994 | Keimel |
| 5,545,186 A | 8/1996 | Olson et al. |
| 5,855,593 A | 1/1999 | Olson et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,480,745 B2 | 11/2002 | Nelson et al. |
| 6,599,250 B2 | 7/2003 | Webb et al. |

(Continued)

*Primary Examiner* — Scott Getzow
(74) *Attorney, Agent, or Firm* — Carol F. Barry

(57) ABSTRACT

An implantable medical device and medical device system for delivering a bi-ventricular pacing therapy that includes a plurality of electrodes to sense a cardiac signal, an emitting device to emit a trigger signal to control delivery of the bi-ventricular pacing, and a processor configured to compare the sensed cardiac signal associated with the delivered bi-ventricular pacing to at least one of an intrinsic beat template and an RV template associated with a morphology of RV-only pacing therapy, determine whether an offset interval associated with the bi-ventricular pacing therapy is set to a maximum offset interval level in response to the comparing, adjust the offset interval in response to the offset interval not being set to the maximum offset interval level, and generate the trigger signal to be emitted by the emitting device to subsequently deliver the bi-ventricular pacing therapy having the adjusted offset interval.

27 Claims, 10 Drawing Sheets

(56) References Cited

U.S. PATENT DOCUMENTS

| | | | |
|---|---|---|---|
| 7,742,812 B2 | 6/2010 | Ghanem et al. | |
| 7,904,153 B2 | 3/2011 | Greenhut et al. | |
| 8,126,553 B2 | 2/2012 | Mayotte | |
| 8,160,684 B2 | 4/2012 | Ghanem et al. | |
| 8,532,785 B1 | 9/2013 | Crutchfield et al. | |
| 8,923,963 B2 | 12/2014 | Bonner et al. | |
| 2004/0158293 A1* | 8/2004 | Yonce | A61B 5/04525 607/9 |
| 2007/0088397 A1* | 4/2007 | Jacobson | A61N 1/3925 607/9 |
| 2014/0121720 A1 | 5/2014 | Bonner et al. | |
| 2015/0321011 A1 | 11/2015 | Carney et al. | |
| 2015/0321012 A1 | 11/2015 | Cinbis et al. | |
| 2016/0015985 A1 | 1/2016 | Cho et al. | |

* cited by examiner

DELIVERY OF BI-VENTRICULAR PACING THERAPY IN A CARDIAC MEDICAL DEVICE AND MEDICAL DEVICE SYSTEM

RELATED APPLICATION

The present application claims priority and other benefits from U.S. Provisional Patent Application Ser. No. 62/199,409, filed Jul. 31, 2015, entitled "CAPTURE MANAGEMENT DURING LV PACING THERAPY IN A CARDIAC MEDICAL DEVICE AND MEDICAL DEVICE SYSTEM", and from U.S. Provisional Patent Application Ser. No. 62/199,424, filed Jul. 31, 2015, entitled "DELIVERY OF LEFT VENTRICULAR PACING THERAPY DURING CARDIAC RESYNCHRONIZATION THERAPY IN A CARDIAC MEDICAL DEVICE AND MEDICAL DEVICE SYSTEM", both incorporated herein by reference in their entireties.

FIELD OF THE DISCLOSURE

The present disclosure pertains to cardiac pacing methods and systems, and, more particularly, to a method and apparatus for delivery of bi-ventricular pacing therapy in a cardiac medical device and medical device system.

BACKGROUND OF THE DISCLOSURE

Implantable pacemakers and implantable cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks. Medical device technology advancement has led toward smaller and smaller implantable devices. Recently, this reduction in size has resulted in the introduction of leadless intracardiac pacemakers that can be implanted directly in a heart chamber. One advantage of a leadless intracardiac device is the elimination of the use of transvenous, intracardiac leads, resulting in the elimination of complications due to infection associated with a lead extending from a subcutaneous pacemaker pocket transvenously into the heart, for example. Other complications such as "twiddler's syndrome", lead fracture or poor connection of the lead to the pacemaker are eliminated as the result of the use of a leadless, intracardiac pacemaker.

Cardiac resynchronization therapy (CRT) is an example of a pacing therapy that includes delivering pacing pulses in a heart chamber at a predetermined time interval after a sensed or paced event in another heart chamber to restore or improve heart chamber synchrony. Improved heart chamber synchrony is expected to alleviate symptoms of heart failure. Achieving a positive clinical benefit from CRT, however, may be dependent on several therapy control parameters, such as the timing intervals used to control pacing pulse delivery, e.g., an atrio-ventricular (AV) interval and/or an inter-ventricular (VV) interval. The AV interval controls the timing of ventricular pacing pulses relative to a preceding atrial depolarization, intrinsic or paced. The VV interval controls the timing of a pacing pulse in one ventricle relative to a paced or intrinsic sensed event in the other ventricle. Pacing may be delivered in the right ventricle (RV) and/or the left ventricle (LV) to restore ventricular synchrony.

Cardiac resynchronization utilizing cardiac ventricular pacing therapy and cardiac pacing devices operate by either delivering pacing stimulus to both ventricles or to one ventricle with the desired result of a more or less simultaneous mechanical contraction and ejection of blood from the ventricles. Triggered pacing systems have been developed for delivery of cardiac synchronization therapy, such as described, for example, in U.S. patent application Ser. No. 14/695,004, to Carney et al. Such triggered pacing systems may include a therapy delivery device, such as a pacing device implanted with the left ventricle, that delivers the ventricular pacing therapy and a sensing device, such as a subcutaneously positionable implantable cardio-defibrillator (ICD), that senses a physiological signal to determine a need for therapy, and generate a control signal passed to a trigger signal emitting device when therapy delivery by the therapy delivery device is required. The trigger signal emitting device emits a trigger signal that is detected by the therapy delivery device, which then delivers at least a portion of a CRT therapy to the patient.

Due to a number of factors associated with a variety of patients, such cardiac pacing systems may not always effectively delivery CRT. For example, factors such as varying capture thresholds, pacing lead and/or electrode migration or dislodgement, time required for appropriate signal processing, confounding conduction delays or conduction blockages, diverse electrode placement locations, inappropriately programmed sensed or paced atrio-ventricular (A-V) or ventriculo-ventricular (V-V) delays, and the like may reduce the effectiveness of CRT.

In either form of CRT delivery, whether fusion-based or the more traditional bi-ventricular stimulation, confirming that pacing stimulus captures the systemic ventricle, which in most cases is the left ventricle (LV), is a very important clinical issue so that the desired benefits of the CRT are in fact delivered to a patient. Ideally, each pacing pulse stimulus delivered to a ventricle evokes a response from the ventricle. The delivery of effective left ventricular pacing helps to ensure that the desired evoked response takes place during delivery of bi-ventricular pacing therapy, and is therefore is an important factor in the delivery of bi-ventricular pacing therapy for cardiac resynchronization therapy (CRT).

DETAILED DESCRIPTION OF EXEMPLARY EMBODIMENTS

Exemplary methods, devices, and systems shall be described with reference to FIGS. 1-9B. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

Figure 1:
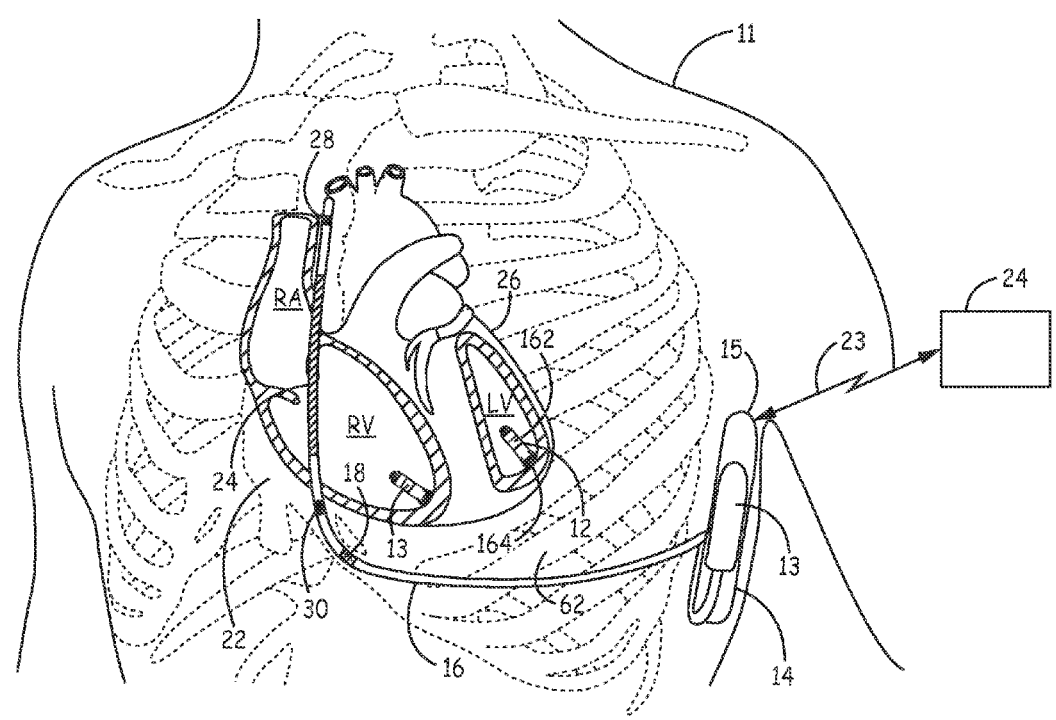
FIG. 1 is a conceptual diagram illustrating an exemplary implantable medical device (IMD) system for delivering bi-ventricular pacing therapy according to an embodiment of the present disclosure.

FIG. 1 is a conceptual diagram illustrating an exemplary implantable medical device (IMD) system for delivering bi-ventricular pacing therapy according to an embodiment of the present disclosure. As illustrated in FIG. 1, according to one embodiment, an implantable medical device (IMD) system 10 for delivering bi-ventricular pacing therapy may include a left ventricular LV pacing device 12, such as a leadless left ventricular LV pacing device, and a right ventricular pacing device 13, such as a leadless right ventricular RV pacing device, for example. Both the LV pacing device 12 and the RV pacing device 13 are capable of delivering cardiac pacing therapy to the heart 26, as described below. In addition, the implantable medical device system 10 includes a cardiac sensing device 14, such as a subcutaneously implantable cardioverter defibrillator ICD coupled to an extravascular defibrillation lead 16. Defibrillation lead 16 includes a defibrillation electrode 24, which may be an elongated coil electrode, and a pair of sensing electrodes 28 and 30, illustrated as ring electrodes but may be or other types of electrodes, and a trigger signal emitting device 18. Trigger signal emitting device 18 includes a transducer that is controlled by the sensing device 14 to emit trigger signals to cause the LV pacing device 12 and the RV pacing device 13 to deliver one or more pacing pulses during bi-ventricular pacing therapy.

Sensing device 14 is shown implanted subcutaneously on the left side of patient 1. Defibrillation lead 16, which is connected to sensing device 14, extends medially from the sensing device 14 toward sternum 22 and xiphoid process 20 of patient 11. At a location near xiphoid process 20 defibrillation lead 16 bends or turns and extends subcutaneously superior, substantially parallel to sternum 22. Defibrillation lead 16 may be implanted such that lead 16 is offset laterally to the left or right side of the body of sternum 22 and may be implanted subcutaneously, e.g., between the skin and the ribs or sternum. Defibrillation lead 16 may be implanted at other locations or angles relative to sternum 22 or positioned further superior or inferior depending on the location of sensing device 14, position of electrodes 24, 28, and 30 and signal emitting device 18 along lead 16 and the location of the LV pacing device 12 and the RV pacing device 13, or other factors. In other instances, lead 16 may be implanted at other extravascular locations. In one example, lead 16 may be implanted at least partially in a substernal location or within ribcage 32, within the thoracic cavity and within or outside the pericardium, not necessarily in direct contact with heart 26.

Defibrillation lead 16 is positioned such that a therapy vector between defibrillation electrode 24 and a second electrode (such as a portion of the housing 15 of sensing device 14 or an electrode placed on a second lead) is substantially across one or both ventricles of heart 26. The therapy vector may, in one example, be viewed as a line that extends from a point on the defibrillation electrode 24 to a point on the housing 15 (sometimes referred to as a "can" electrode) of sensing device 14. In another example, defibrillation lead 16 may be placed along sternum 22 such that a therapy vector between defibrillation electrode 18 and housing 15 (or other electrode) is substantially across an atrium of heart 26. In this case, system 10 may be used to provide atrial therapies, such as therapies to treat atrial fibrillation.

Trigger signal emitting device 18 is positioned to establish a signal transmission pathway that does not excessively attenuate the trigger signal transmitted from emitting device 18 to a receiver or detector included in intracardiac the LV pacing device 12 and the RV pacing device 13. For example, the location of emitting device 18 may be selected so that a direct optical pathway between emitting device 18 and the LV pacing device 12 and the RV pacing device 13 avoids highly reflective or light attenuating tissues as much as possible. When lead 16 is positioned extra-thoracically, emitting device 18 may be positioned inferior to the xyphoid process 20 in a position approximately as shown. In other examples, emitting device 18 is positioned relative to the LV pacing device 12 and the RV pacing device 13 to establish an efficient transmission pathway that takes into account the properties of the surrounding and intervening tissues.

Although sensing device 14 is illustrated as being implanted near a midaxillary line of patient 11, sensing device 14 may also be implanted at other subcutaneous locations on patient 11, such as further posterior on the torso toward the posterior axillary line, further anterior on the torso toward the anterior axillary line, in a pectoral region, or at other locations of patient 11. In instances in which sensing device 14 is implanted pectorally, lead 16 would follow a different path, e.g., across the upper chest area and inferior along sternum 22. When the sensing device 14 is implanted in the pectoral region, the system 10 may include a second lead including a defibrillation electrode, and optionally an emitting device, that extends along the left side of the patient such that the defibrillation electrode of the second lead is located along the left side of the patient to function as an anode or cathode of the therapy vector for defibrillating heart 26.

Sensing device 14 includes a housing 15 that forms a hermetic seal that protects components within the sensing device 14. Housing 15 may enclose one or more components, including processors, memories, transmitters, receivers, sensors, sensing circuitry, therapy circuitry and other appropriate components (often referred to herein as modules). The housing 15 of sensing device 14 may be formed of a conductive material, such as titanium or other biocompatible conductive material or a combination of conductive and non-conductive materials. In some instances, the housing 15 functions as an electrode (sometimes referred to as a housing electrode or can electrode) that is used in combination with one of electrodes 24, 28 and 30 to deliver a therapy to heart 26 or to sense electrical activity of heart 26.

Sensing device 14 may include a connector assembly 13 (sometimes referred to as a connector block or header) for receiving a proximal connector (not illustrated) of lead 16. Connector assembly 13 includes electrical feedthroughs through which electrical connections are made between conductors within defibrillation lead 16 and electronic components included within the housing 15. Depending on the intended implant location of sensing device 14, an emitting device 18 may be included in connector assembly 13 and/or housing 15 in addition to or in place of the emitting device 18 carried by lead 16 for transmitting trigger signals to the LV pacing device 12 and the RV pacing device 13. For example, an emitting device may be embedded, e.g. overmolded, in the connector assembly or included in a wafer-scale hermetic package incorporated in connector assembly 13 and coupled to feedthroughs extending into housing 15 for receiving control signals from ICD internal circuitry.

Lead 16 may include a connector at the proximal end of lead 16, such as a DF4 connector, bifurcated connector (e.g., DF-1/IS-1 connector), or other type of connector having at least one terminal pin that couples to a port within the connector assembly 13 of sensing device 14. The lead body of defibrillation lead 16 may be formed from a non-conductive material, including silicone, polyurethane, fluoropolymers, mixtures thereof, and other appropriate materials, and shaped to form one or more lumens within which the one or more elongated conductors extend.

Defibrillation lead 16 includes elongated electrical conductors (not illustrated) that each extend within the elongated lead body from the connector on the proximal end of defibrillation lead 16 to respective electrodes 24, 28 and 30 and emitting device 18. Although defibrillation lead 16 is illustrated as including three electrodes 24, 28 and 30, defibrillation lead 16 may include more or fewer electrodes. When the connector of defibrillation lead 16 is connected to connector assembly 13, the respective conductors may electrically couple to circuitry, such as a therapy delivery module or a sensing module, or a trigger signal drive signal circuit of sensing device 14 via connections in connector assembly 13, including associated feedthroughs. The electrical conductors transmit electrical stimulation pulses from a therapy module within the sensing device 14 to one or more of electrodes 24, 28 and 30 and transmit sensed electrical signals from one or more of electrodes 24, 28 and 30 to the sensing module within the sensing device 14. An electrical conductor extending from the proximal lead connector to emitting device 18 conducts a control signal to emitting device 18 to cause emitting device 18 to emit a trigger signal at appropriate times for causing the LV pacing device 12 and the RV pacing device 13 to deliver one or more pacing pulses to heart 26.

Sensing device 14 may sense electrical activity of heart 26 via one or more sensing vectors that include combinations of electrodes 28 and 30 and housing 15. For example, sensing device 14 may obtain cardiac electrical signals using a sensing vector between electrodes 28 and 30, between electrode 28 and the conductive housing 15, between electrode 30 and housing 15, or any combination thereof. In some instances, sensing device 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15.

Sensing device 14 determines a need for pacing therapy in response to the sensed cardiac electrical signals, which may include P-waves and R-waves for example, and controls emitting device 18 to emit trigger signals based on that determination. The need for pacing pulses may be determined according to programmed single chamber, dual chamber or multi-chamber bradycardia or CRT control parameters other cardiac pacing therapy parameters. Sensing device 14 may also analyze the sensed electrical signals to detect tachycardia, such as ventricular tachycardia or ventricular fibrillation, and in response to detecting tachycardia may generate and deliver an electrical therapy to heart 26. For example, sensing device 14 may deliver one or more defibrillation shocks via a therapy vector that includes defibrillation electrode 24 and the housing 15.

Electrodes 24, 28, 30 and housing 15 may be used for sensing ECG signals for use in controlling the timing of an R-wave synchronized shock delivered by sensing device 14 and for controlling timing of pacing pulses delivered by the LV pacing device 12 and the RV pacing device 13. In some instances, one or more pacing therapies may be delivered prior to or after delivery of a defibrillation shock by sensing device 14, such as anti-tachycardia pacing (ATP) or post shock pacing. In these instances, sensing device 14 may generate and deliver pacing pulses via therapy vectors that include electrodes 24, 28, 30 and/or housing 15. Alternatively, sensing device 14 may cause emitting device 18 to emit trigger signals to cause the LV pacing device 12 and the RV pacing device 13 to deliver pacing pulses to heart 26 at appropriate times when ATP or post-shock pacing is needed as well as for bradycardia or CRT pacing therapies, such as bi-ventricular pacing, is needed.

The example sensing device 14 illustrated in FIG. 1 is illustrative in nature and should not be considered limiting of the sensing device used in a triggered therapy delivery system and associated techniques described in this disclosure. For instance, in addition to sensing ECG signals, sensing device 14 may include shock therapy capabilities only without pacing therapy capabilities. In other examples, sensing device 14 may be coupled to more than one lead for sensing ECG signals and/or sending trigger signals to the LV pacing device 12 and/or the RV pacing device 13. In still other examples, a sensing device may be substituted for sensing device 14 that is a single chamber or dual chamber subcutaneous pacemaker without cardioversion/defibrillation capabilities or a sensing-only device without therapy delivery capabilities, for example. Any of these sensing devices may be coupled to housing-based electrodes and/or electrodes carried by a transvenous, intracardiac or extravascular, extracardiac lead for sensing a cardiac electrical signal and determining appropriate times for triggering the LV pacing device 12 and the RV pacing device 13 to delivery therapy.

LV pacing device 12 and the RV pacing device 13 are transcatheter, intracardiac pacemakers adapted for implantation wholly within a heart chamber, e.g. wholly within the RV, wholly within the LV, wholly within the right atrium (RA) or wholly within the left atrium (LA) of heart 26. In the example of FIG. 1, the LV pacing device 12 is positioned proximate to an inner wall of the LV to provide left ventricular and the RV pacing device 13 is positioned proximate to an inner wall of the right ventricle to provide right ventricular pacing.

LV pacing device 12 and the RV pacing device 13 are capable of producing electrical pacing pulses delivered to heart 26 via one or more electrodes 162 and 164 located on the outer housing of the LV pacing device 12 and the RV pacing device 13. LV pacing device 12 and the RV pacing device 13 include a detector 212 (shown in FIG. 2) for receiving a trigger signal emitted by emitting device 18. In response to detecting a trigger signal, the LV pacing device 12 and the RV pacing device 13 deliver one or more pacing pulses.

In one embodiment, the LV pacing device 12 and the RV pacing device 13 each include a pulse generator configured to deliver one or more pacing pulses upon receiving a trigger signal from emitting device 18. LV pacing device 12 and the RV pacing device 13 may not be configured to sense cardiac signals, so that cardiac signal sensing is performed by sensing device 14, which senses ECG signals through lead 16 and controls pacing delivered by the LV pacing device 12 and the RV pacing device 13 via trigger signals emitted by emitting device 18 under the control of the sensing device 14. Therefore, LV pacing device 12 and the RV pacing device 13 may rely solely on a trigger signal from emitting device 18 for controlling the timing of bi-ventricular pacing pulse delivery. In this way, cardiac signal sensing and radio frequency telemetry functions may be omitted such that the LV pacing device 12 and the RV pacing device 13 include a pulse generator with limited memory, processing, and other functions directed to therapy delivery, minimizing the size of the LV pacing device 12 and the RV pacing device 13.

In other embodiments, the LV pacing device 12 and the RV pacing device 13 sense EGM signals in the heart chamber in which it is implanted. Since the LV pacing device 12 and the RV pacing device 13 are positioned wholly within a heart chamber, the EGM signal sensed by the LV pacing device 12 and the RV pacing device 13 will be less sensitive or insensitive to P-waves and/or R-waves occurring in other heart chambers. In past practice, a subcutaneous pacemaker might be coupled to one or more leads that position sense electrodes in or along multiple heart chambers such that multiple sensing channels can be monitored. By monitoring multiple sensing channels, coordinated pacing pulses can be delivered to one or more heart chambers at specified time intervals, e.g., AV or VV intervals.

FIG. 1 further depicts a programmer 24 in wireless communication with cardiac sensing device 14 via a communication link 23. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other caregiver, or patient, may interact with programmer 24 to communicate with cardiac sensing device 14. For example, the user may interact with programmer 24 to retrieve physiological or diagnostic information from cardiac sensing device 14. A user may also interact with programmer 24 to program cardiac sensing device 14, e.g., select values for operational parameters of the cardiac sensing device 14, including parameters used to control a trigger emitting device positioned along the sensing device 14 to emit a trigger signal for controlling therapy delivery device 12. A user may use programmer 24 to retrieve information from cardiac sensing device 14 regarding the rhythm of heart 20, heart rhythm trends over time, or arrhythmic episodes.

As indicated, cardiac sensing device 14 and programmer 24 communicate via wireless communication 23. Examples of communication techniques may include low frequency or radiofrequency (RF) telemetry, but other techniques may be used. In some examples, programmer 24 may include a programming head that is placed proximate to the patient's body near the cardiac sensing device 14 implant site in order to improve the quality or security of communication between cardiac sensing device 14 and programmer 24.

Figure 2:
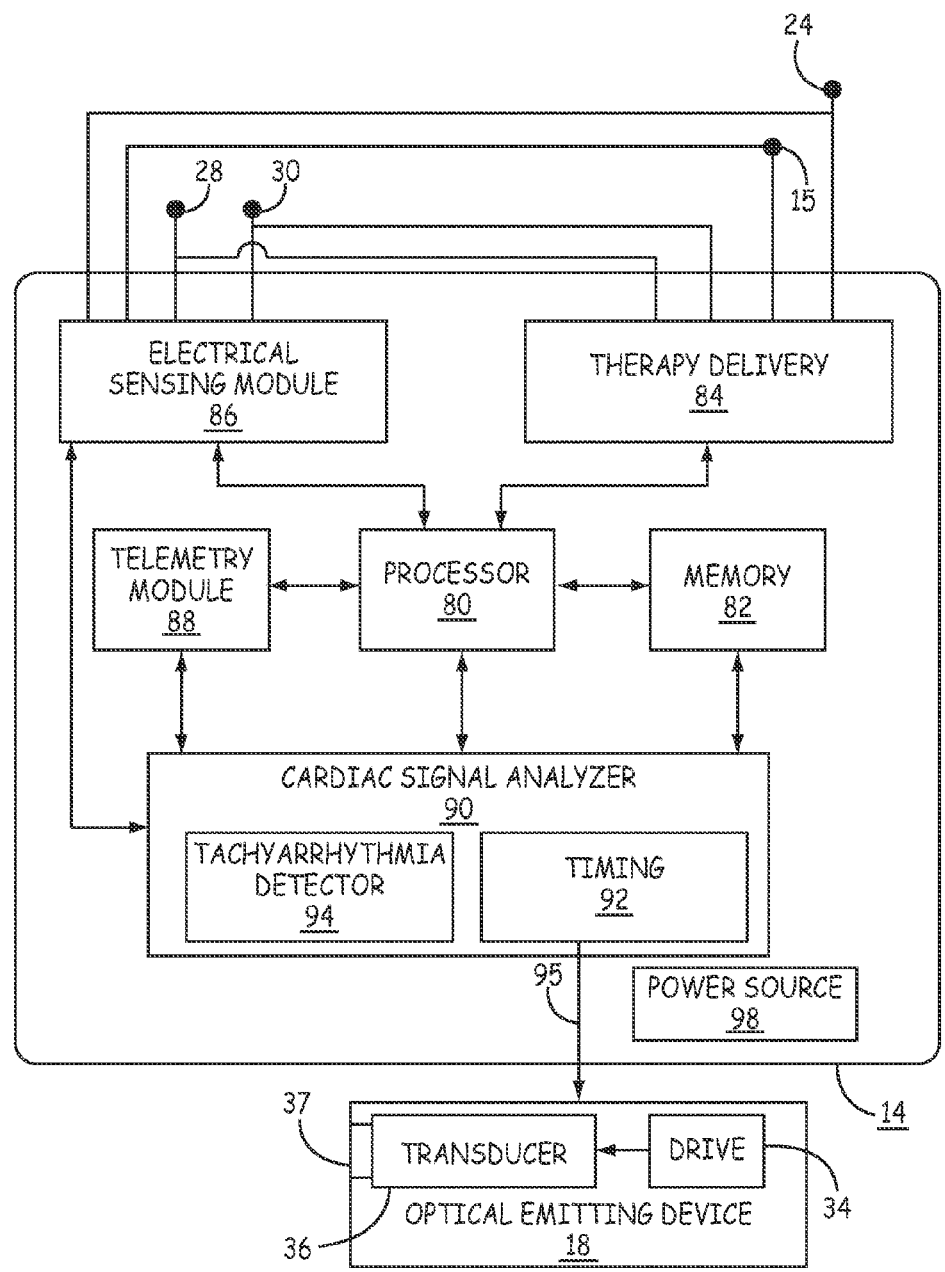
FIG. 2 is a functional block diagram of an exemplary sensing device of the implantable medical device (IMD) system of FIG. 1.

FIG. 2 is a functional block diagram of an exemplary sensing device of the implantable medical device (IMD) system of FIG. 1. As illustrated in FIG. 2, sensing device 14 includes processing and control module 80, also referred to herein as "control module" 80, memory 82, therapy delivery module 84, electrical sensing module 86, telemetry module 88 and cardiac signal analyzer 90. A power source 98 provides power to the circuitry of sensing device 14, including each of the modules 80, 82, 84, 86, 88, and 90. Power source 98 may include one or more energy storage devices, such as one or more chargeable or non-re-chargeable batteries.

The functional blocks shown in FIG. 2 represent functionality that may be included in sensing device 14 and may include any discrete and/or integrated electronic circuit components that implement analog and/or digital circuits capable of producing the functions attributed to sensing device 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, memory devices, etc. Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to sensing device 14. The non-transitory computer readable media storing the instructions may include any of the media listed above, with the sole exception being a transitory propagating signal. The particular form of software, hardware and/or firmware employed to implement the functionality disclosed herein will be determined primarily by the particular system architecture employed in the IMD system devices. Providing software, hardware, and/or firmware to accomplish the described functionality in the context of any modern IMD system, given the disclosure herein, is within the abilities of one of skill in the art.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, cardiac signal monitoring may be performed by cardiac signal analyzer 90 for determining a need for therapy delivered by sensing device 14 and/or the LV pacing device 12 and the RV pacing device 13 or implemented in control module 80 executing instructions stored in memory 82. In this way, the capture threshold management process and the morphology analysis, described below, may be performed by either the cardiac signal analyzer 90 or the control module 80, or by a combination of the cardiac signal analyzer 90 and the control module 80.

Processing and control module 80 communicates with therapy delivery module 84, cardiac signal analyzer 90 and sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16 as shown in FIG. 1 and housing 15, at least a portion of which also serves as a common or ground electrode.

Electrical sensing module 86 is coupled to electrodes 28 and 30 in order to monitor electrical activity of the patient's heart. Electrical sensing module 86 may optionally be coupled to electrodes 24 and 15 and enabled to selectively monitor one or more sensing vector selected from the available electrodes 24, 28, 30 and 15. For example, sensing module 86 may include switching circuitry for selecting which of electrodes 24, 28, 30 and housing electrode 15 are coupled to sense amplifiers included in sensing module 86. Switching circuitry may include a switch array, switch matrix, multiplexer, or any other type of switching device suitable to selectively couple sense amplifiers to selected electrodes. A sensing vector between electrodes 28 and 30 may be selected for sensing an ECG signal or sensing vector may be selected that utilizes coil electrode 24 and/or housing 15, e.g., from sensing electrode 28 to housing 15 or from sensing electrode 30 to housing 15.

One or more ECG signals are passed to the input of sensing module 86, which includes one or more sense amplifiers or other cardiac event detection circuitry for sensing cardiac events, e.g., P-wave and/or R-waves, from the ECG signal(s). Sensing module 86 includes sense amplifiers that pass sense event signals to cardiac signal analyzer 90. For example P-wave sense signals and R-wave sense signals are passed to cardiac signal analyzer 90 when the ECG signal crosses a respective P-wave sensing threshold and R-wave sensing threshold, which may each be auto-adjusting sensing thresholds. Bradycardia or asystole is typically determined by a pacing escape interval timer expiring within the timing circuit 92. In response to the pacing escape interval expiring, a control signal 95 is passed to the emitting device 18. The pacing escape interval is restarted upon a pacing pulse trigger or a sense event signal. Other pacing intervals, such AV or VV pacing intervals are started by control module 80 upon sensing an event in one cardiac chamber, atrial or ventricular, and sending a trigger signal to the LV pacing device 12 and the RV pacing device 13 to deliver a pacing pulse synchronized to the sensed event at the AV or VV interval.

The control signal 95 in the illustrative examples presented herein may be referred to as a pacing control signal because it causes the LV pacing device 12 and the RV pacing device 13 to deliver a pacing pulse to a heart chamber. In other examples, the control signal 95 may be produced by cardiac signal analyzer 90 to cause other types of therapy pulses to be delivered by a therapy delivery device such as a leadless cardiac pacemaker. For example control signal 95 may be produced to cause the pacemaker or another therapy delivery device to deliver an ATP pulse, a vagal nerve stimulation pulse, or other type of electrical stimulation pulse.

The control signal 95 is an electrical signal that is passed to emitting device 18 along lead 16 (or another lead carrying emitting device 18) when emitting device is coupled to sensing device 14 in a wired connection. The control signal 95 is alternatively an electrical signal that is passed to telemetry module 88 where it is converted to a wireless telemetry signal that is transmitted via telemetry module 88, to emitting device 18. Emitting device 18 may be carried by a lead but configured to wirelessly receive a control signal 95 from telemetry module 88. Alternatively, the emitting device is not a lead-based emitting device, and may be located within the sensing device 14.

Trigger signal emitting device 18 includes a drive signal circuit 34 that receives the control signal 95, either as a wired electrical signal or a wireless signal from telemetry module 88. It is understood that in some embodiments, drive signal circuit 34 may be included within the housing 15 of sensing device 14 and coupled to a transducer 36 located external to housing 15.

Drive signal circuit 34 passes an electrical signal to a transducer 36 to enable the transducer 36 to emit a trigger signal. As described herein, the trigger signal is received and detected by the LV pacing device 12 and the RV pacing device 13 to cause the LV pacing device 12 and the RV pacing device 13 to deliver one or more pacing pulses to the patient's heart, such as delivery of bi-ventricular pacing, as described below. The trigger signal may be generated according to pre-set intensity, wavelength, and signal duration and other signal characteristics. In other words, the control signal may only signal the emitting device 18 that a trigger signal is needed. The trigger signal merely signals the LV pacing device 12 and the RV pacing device 13 to delivery therapy without signaling any information relating to how many pacing pulses, what pulse amplitude or pulse width or other pacing pulse control parameter information. The LV pacing device 12 and the RV pacing device 13 may be programmed to deliver a predetermined number of pacing pulses according to predefined pulse control parameters when the trigger signal is detected.

Alternatively, control signal 95 may include encoded pacing pulse control information. The control signal generated by drive signal circuit 34 may cause transducer 36 to emit a trigger signal according to an intensity, wavelength, signal duration and/or other characteristic of the trigger signal that is intentionally adjusted according to the control signal. In this case, the control signal 95 signals the emitting device 18 that a trigger signal is needed as well as what characteristic(s) the emitted trigger signal should have. The control signal generated by drive circuit 34 may cause transducer 36 to emit a trigger signal according to a frequency, duration, amplitude or other intentionally varied characteristics of the trigger signal to include pacing pulse control parameter information. As described below, a parameter of the trigger signal emitted by transducer 36 may be controllably varied by control signal 95 and drive circuit 34 to cause therapy delivery device, i.e., the LV pacing device 12 and the RV pacing device 13, to adjust a pacing pulse control parameter such as pacing pulse width, pulse number, LV pre-excitation or offset interval, a V-V interval, etc. Trigger signal parameters that may be varied under the control of signal and drive circuit 34 include, without limitation, trigger signal amplitude, signal frequency, pulse width, pulse number and interpulse interval. The LV pacing device 12 and the RV pacing device 13 may be configured to detect the characteristic(s) of the emitted trigger signal and set a pacing pulse control parameter based on that characteristic.

Timing circuit 92 may generate the control signal 95 to trigger LV pacing device 12 and the RV pacing device 13 to deliver pacing pulses to provide bi-ventricular pacing, bradycardia pacing, atrial-synchronized ventricular pacing, ATP, CRT, AV nodal stimulation, or other pacing therapies according to pacing algorithms and timing intervals stored in memory 82. It is understood that although the trigger emitting device is shown as being positioned along the lead 16, trigger emitting device 18 may be included as part of the device circuitry located within the device housing 15 of the sensing device 14.

Cardiac signal analyzer 90 includes a tachyarrhythmia detector 94 for detecting and discriminating supraventricular tachycardia (SVT), ventricular tachycardia (VT) and ventricular fibrillation (VF). Some aspects of sensing and processing subcutaneous ECG signals are generally disclosed in commonly-assigned U.S. Pat. No. 7,904,153 to Greenhut, et al., hereby incorporated herein by reference in its entirety. The timing of R-wave sense signals from sensing module 86 is used by tachyarrhythmia detector 94 to measure R-R intervals for counting RR intervals in different detection zones or determining a heart rate or other rate-based measurements for detecting ventricular tachyarrhythmia. Electrical sensing module 86 may additionally or alternatively provide digitized ECG signals to cardiac signal analyzer 120 for use in detecting tachyarrthmias. Examples of ICDs that may be adapted for use with a triggered pacemaker 12 and operations that may be performed by tachyarrhythmia detector 94 for detecting, discriminating and treating tachyarrhythmia are generally disclosed in U.S. Pat. No. 7,742,812 to Ghanem, et al., U.S. Pat. No. 8,160,684 to Ghanem, et al., U.S. Pat. No. 5,354,316 to Keimel; U.S. Pat. No. 6,393,316 to Gillberg et al., U.S. Pat. No. 5,545,186 to Olson, et al., and U.S. Pat. No. 5,855,593 to Olson, et al., all of which patents are incorporated herein by reference in their entirety. As mentioned above, the capture threshold management process and the morphology analysis, described below, may be performed by either the cardiac signal analyzer 90 or the control module 80, or by a combination of the cardiac signal analyzer 90 and the control module 80

Telemetry module 88 includes a transceiver and antenna for communicating with another device, such as an external programmer 40 and emitting device 18 when it is configured as a wireless device. Under the control of control processor 80, telemetry module 88 may receive downlink telemetry from and send uplink telemetry to programmer 40 or other external device. Telemetry module 88 may transmit a control signal 95 wirelessly to emitting device 18, e.g., as an RF signal.

Figure 3:
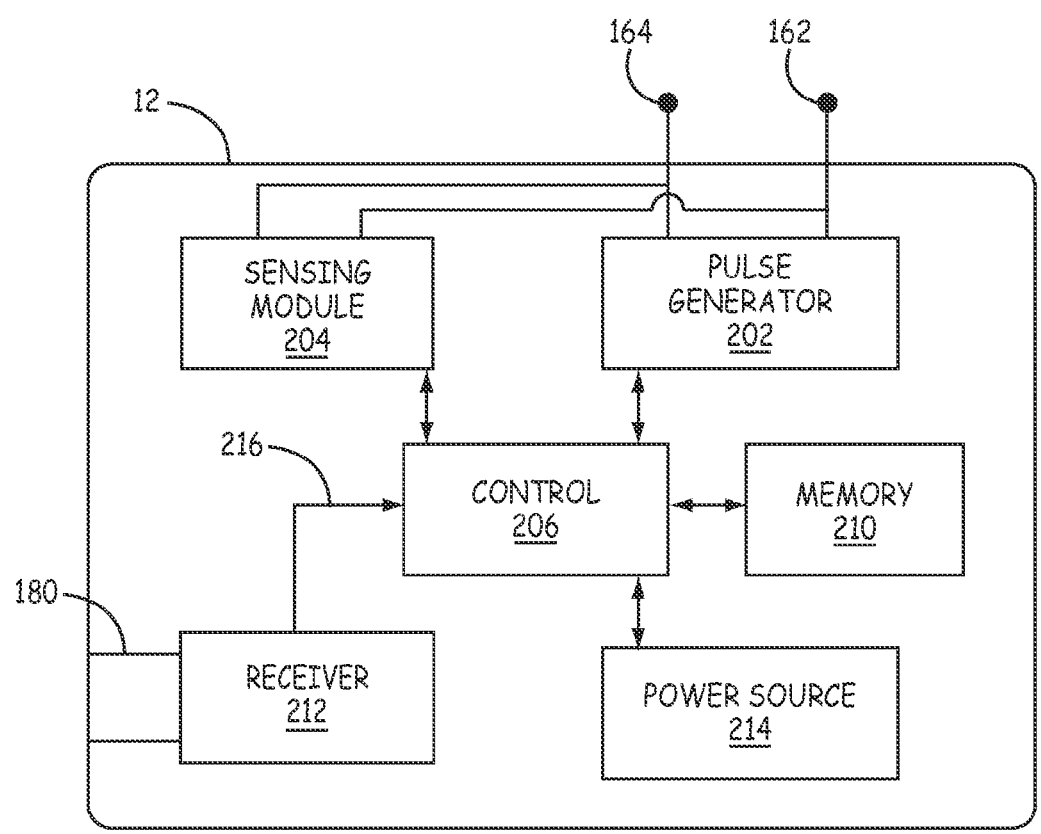
FIG. 3 is a functional block diagram of an example configuration of a leadless pacing device of an implantable device system according to an embodiment of the present disclosure.

FIG. 3 is a functional block diagram of an example configuration of a leadless pacing device of an implantable device system according to an embodiment of the present disclosure. As illustrated in FIG. 3, LV pacing device 12 and RV pacing device 13 each include a pulse generator 202, an optional sensing module 204, a control module 206, memory 210, trigger signal receiver 212 and a power source 214. Pulse generator 202 generates electrical stimulation pulses that are delivered to heart tissue via electrodes 162 and 164 of LV pacing device 12 and RV pacing device 13. Control module 206 controls pulse generator 202 to deliver a stimulation pulse in response to receiving a trigger detect (TD) signal 216 from receiver 212. In other embodiments, pulse generator 202 may be configured to be enabled to deliver a stimulation pulse directly by an input signal received from receiver 212. For example, a switch responsive to a trigger detect signal 216 produced by receiver 212 may enable pulse generator 202 to deliver a stimulation pulse to a targeted tissue via electrodes 162 and 164 positioned on the LV pacing device 12 and RV pacing device 13.

Pulse generator 202 includes one or more capacitors and a charging circuit to charge the capacitor(s) to a pacing pulse voltage. The pacing capacitor may be charged to the pacing pulse voltage while control module 206 waits for a trigger detect signal 216 from receiver 212. Upon detecting the trigger signal, the capacitor is coupled to pacing electrodes 162, 164 to discharge the capacitor voltage and thereby deliver the pacing pulse. Alternatively, detection of the trigger signal initiates pacing capacitor charging and when a predetermined pacing pulse voltage is reached, the pulse is delivered. Pacing circuitry generally disclosed in U.S. Pat. No. 8,532,785 (Crutchfield), hereby incorporated herein by reference in its entirety, may be implemented in the LV pacing device 12 and RV pacing device 13 for charging a pacing capacitor to a predetermined pacing pulse amplitude under the control of control module 206 and delivering a pacing pulse.

Alternatively, pulse generator 202 may include a switch that connects power source 214 to pacing electrodes 162 and 164 to deliver the pacing pulse. The switch is opened by trigger detect signal 216 or by a control signal from control module 206, and power source 214 delivers energy to pulse generator 202 for generating a pacing pulse.

Control module 206 may determine a pacing pulse control parameter from the trigger detect signal 216 and use the determined pacing pulse control parameter to control pulse generator 202 to deliver one or more pacing pulses in accordance with the determined control parameter, as described below. For example, the pulse width or other aspect of the trigger signal may be determined by control module 206 and used to set the pulse width (or another aspect) of the pacing pulse.

Receiver 212 receives trigger signals through coupling member 180. Receiver 212 includes one or more receiving transducers, which may be mounted directly along an inner surface of coupling member 180, e.g., for receiving the trigger signal, which may be sound waves, RF or light. The trigger signal causes a receiving transducer to produce a voltage signal that is passed to a comparator included in receiver 212 (or control module 206) for comparison to a trigger signal detection threshold. If the voltage signal produced by the receiving transducer is greater than the detection threshold, a trigger detect signal 216 is passed to control module 206, or directly to pulse generator 202, to cause pacing pulse delivery.

Control module 206 controls pulse generator 202 to deliver a pacing pulse according to therapy delivery control parameters such as pulse amplitude, pulse width, pulse number, etc., which may be stored in memory 210. In some examples, pulse generator 202 is enabled to deliver a pacing pulse immediately upon receiving a trigger detect signal 216, either directly from receiver 212 or via control module 206. Alternatively, the pacing pulse may be delivered after a predetermined time delay.

Receiver 212 may include multiple receiving transducers for sensing the trigger signal. The voltage signal produced by multiple transducers may be summed, for example, for comparison to a trigger signal detection threshold. In some embodiments, multiple receiving transducers may be included that are responsive to different frequency bandwidths. Providing detection of different signal frequencies may enable different trigger signals to be transmitted for causing therapy delivery device to perform different pacing functions and/or improve trigger signal detection.

Power source 214 provides power to each of the other modules and components of pacemaker 12 as required. Control module 206 may execute power control operations to control when various components or modules are powered to perform various pacemaker functions. Power source 214 may include one or more energy storage devices, such as one or more rechargeable or non-rechargeable batteries.

Circuitry represented by the block diagram shown in FIG. 3 may include any discrete and/or integrated electronic circuit components that implement analog and/or digital circuits capable of producing the functions attributed to therapy delivery device 12 herein. The functions attributed to therapy delivery device 12 herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), state machine, or equivalent discrete or integrated logic circuitry. Depiction of different features of LV pacing device 12 and RV pacing device 13 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components, which may include combinational or sequential logic circuits, state machines, memory devices, etc.

Memory 210 may include computer-readable instructions that, when executed by control module 206, cause control module 206 to perform various functions attributed throughout this disclosure to LV pacing device 12 and RV pacing device 13. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to detection of a trigger signal received by receiver 212. Examples of a leadless pacing device may be as described for example in U.S. Pat. No. 8,923,963 to Bonner et al., or in U.S. Patent Publication No. 2014/0121720 to Bonner et al., both of which are incorporated herein by reference in their entireties.

Figure 4:
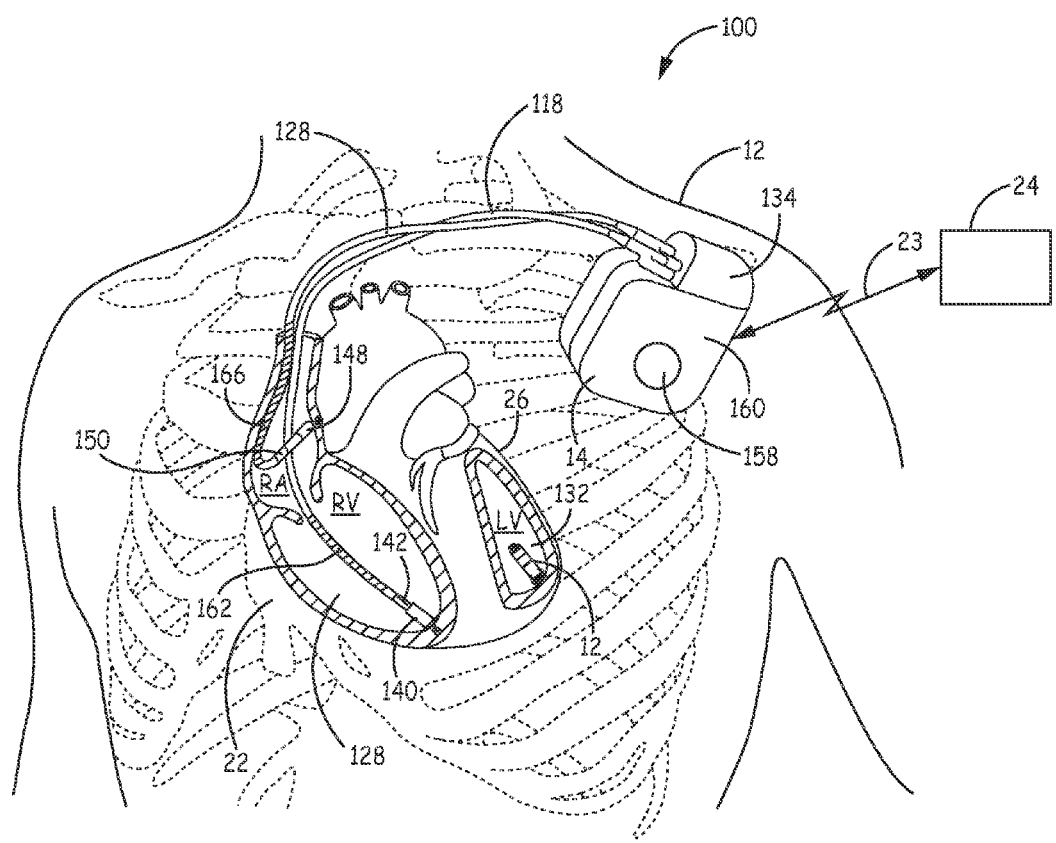
FIG. 4 is a conceptual diagram illustrating an exemplary implantable medical device (IMD) system for delivering bi-ventricular pacing therapy according to an embodiment of the present disclosure.

FIG. 4 is a conceptual diagram illustrating an exemplary implantable medical device (IMD) system for delivering bi-ventricular pacing therapy according to an embodiment of the present disclosure. As illustrated in FIG. 4, according to one embodiment, an implantable medical device (IMD) system 10 for delivering bi-ventricular pacing therapy includes a left ventricular LV pacing device 12, such as a leadless left ventricular LV pacing device and a sensing device 14, such as an implantable pacemaker, implantable cardioverter and/or defibrillator that provides electrical signals to heart 112 via electrodes coupled to one or both of leads 118 and 122. Cardiac sensing device 14, which is shown in FIG. 4 as being an implantable cardioverter defibrillator (ICD), is capable of delivering at least single chamber ventricular pacing in the right ventricle, and, in the embodiment shown, is configured for multi-chamber pacing and sensing in the right atrium (RA) 126 and the right ventricle (RV) 128 using leads 118 and 122.

Cardiac sensing device 14 may deliver RV pacing pulses and sense RV intracardiac EGM signals using RV tip electrode 140 and RV ring electrode 142. RV lead 118 is shown to carry a coil electrode 162 which may be used for delivering high voltage cardioversion or defibrillation shock pulses.

Cardiac sensing device 14 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. Sensing device 14 may detect arrhythmias of a heart 26, such as fibrillation of ventricles 128 and 132, and deliver defibrillation therapy to heart 26 in the form of electrical pulses. According to an embodiment of the present disclosure, sensing device is capable of delivering bi-ventricular pacing therapy in combination with LV pacing device 12, as described below in detail.

Sensing device 14 includes internal circuitry for performing the functions attributed to sensing device 14, and a housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations. Sensing device 14 includes a connector block 134 having connector bores for receiving proximal lead connectors of leads 118 and 122. Electrical connection of electrodes carried by leads 118 and 122 and IMD internal circuitry is achieved via various connectors and electrical feedthroughs included in connector block 134.

Sensing device 14 is configured for delivering CRT therapy, which may include the use of electrodes 140 and 142 and the LV pacing device 12 for delivery of pacing therapy, including bi-ventricular pacing therapy, for example, for controlling and improving ventricular synchrony, as described below in detail.

FIG. 4 further depicts a programmer 24 in wireless communication with cardiac sensing device 14 via a communication link 23. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other caregiver, or patient, may interact with programmer 24 to communicate with cardiac sensing device 14. For example, the user may interact with programmer 24 to retrieve physiological or diagnostic information from cardiac sensing device 14. A user may also interact with programmer 24 to program cardiac sensing device 14, e.g., select values for operational parameters of the cardiac sensing device 14, including parameters used to control a trigger emitting device positioned along the sensing device 14 to emit a trigger signal for controlling therapy delivery device 12. A user may use programmer 24 to retrieve information from cardiac sensing device 14 regarding the rhythm of heart 20, heart rhythm trends over time, or arrhythmic episodes.

As indicated, cardiac sensing device 14 and programmer 24 communicate via wireless communication 23. Examples of communication techniques may include low frequency or radiofrequency (RF) telemetry, but other techniques may be used. In some examples, programmer 24 may include a programming head that is placed proximate to the patient's body near the cardiac sensing device 14 implant site in order to improve the quality or security of communication between cardiac sensing device 14 and programmer 24. Remote patient management systems may be configured to utilize the presently disclosed techniques to enable a clinician to review cardiac signal data and authorize programming of IMD pace control parameters. Reference is made to commonly-assigned U.S. Pat. No. 6,599,250 to Webb et al., U.S. Pat. No. 6,442,433 to Linberg et al., U.S. Pat. No. 6,418,346 to Nelson et al., and U.S. Pat. No. 6,480,745 to Nelson et al. for general descriptions and examples of network communication systems for use with implantable medical devices for remote patient monitoring and device programming.

Figure 5:
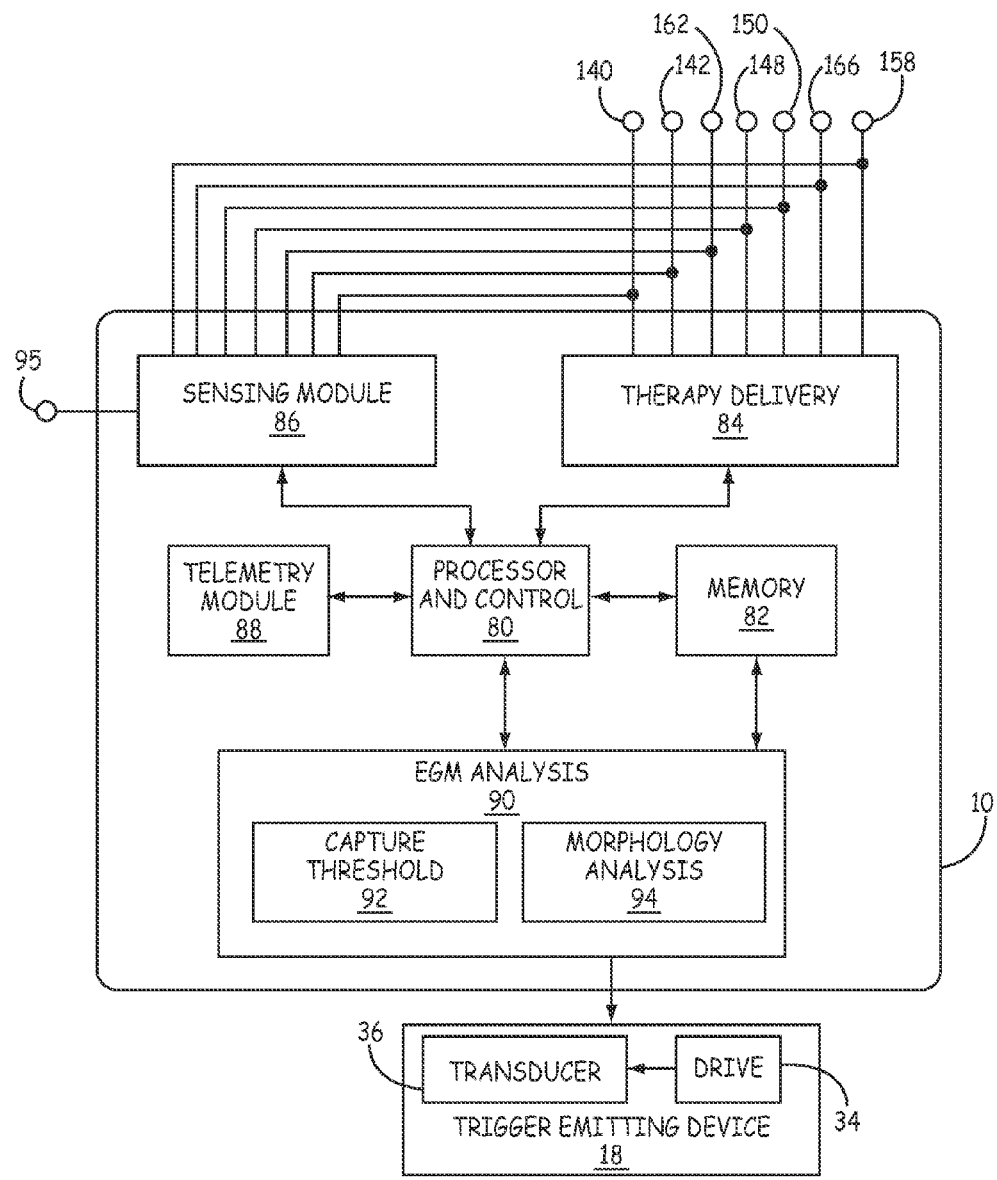
FIG. 5 is a functional block diagram of an exemplary sensing device of the implantable medical device (IMD) system of FIG. 4.

FIG. 5 is a functional block diagram of an exemplary sensing device of the implantable medical device (IMD) system of FIG. 4. As illustrated in FIG. 5, the sensing device 14 includes a processor and control unit 80, memory 82, signal generator 84, sensing module 86, and telemetry module 88. IMD 10 further includes EGM signal analysis module 90, which itself may include a capture threshold detection module 92 and an EGM morphology analysis module 94.

Memory 82 may include computer-readable instructions that, when executed by processor 80, cause sensing device 14 and processor 80 to perform various functions attributed throughout this disclosure to sensing device 14, processor 80, sensing module 86, and EGM analysis module 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, EGM analysis module 90 may, at least in part, be stored or encoded as instructions in memory 82 that are executed by processor and control 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 148, 150, 158, 162, and 166 (all of which are shown in FIG. 4), e.g., via conductors of the respective leads 118 and 122, or, in the case of housing electrode 158, via an electrical conductor disposed within housing 160 of sensing device 14. Signal generator 84 is configured to generate and deliver electrical stimulation therapy to heart 26 via selected combinations of electrodes 140, 142, 148, 150, 158, 162, and 166. Processor and control 80 controls signal generator 84 to deliver cardiac pacing pulses according to atrial-ventricular (AV) and/or inter-ventricular (VV) timing intervals.

Signal generator 84 may include a switch module (not shown) and processor and control 80 may use the switch module to select, e.g., via a data/address bus, which of the available electrodes are used to deliver pacing pulses. Processor 80 may also control which of electrodes 140, 142, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors cardiac signals from electrodes 140, 142, 148, 150, 158, 162, or 166 in order to monitor electrical activity of heart 26. Sensing module 86 may also include a switch module to select which of the available electrodes are used to sense the cardiac activity. In some examples, processor 80 selects the electrodes to function as sense electrodes, or the sensing vector, via the switch module within sensing module 86.

Sensing module 86 includes multiple detection channels, each of which may be selectively coupled to respective combinations of electrodes 140, 142, 148, 150, 158, 162, or 166 to detect electrical activity of a particular chamber of heart 26. Each detection channel may comprise an amplifier that outputs an indication to processor 80 in response to sensing of a cardiac depolarization, in the respective chamber of heart 112. In this manner, processor 80 may detect the occurrence of R-waves and P-waves in the various chambers of heart 26. The occurrence of R-waves sensed using a local bipolar sensing electrode pair is used in measuring relative activation times with respect to different candidate pacing sites for use in selecting a pacing site.

Sensing module 86 may provide an R-wave sense signal to EGM analysis module 90 indicating the time of sensed R-wave. EGM processing module 90 receives the R-wave sense signal and a far-field EGM signal and the timing of the R-wave sense signal relative to the far-field QRS complex. Sensing module 86 may further include digital signal processing circuitry for providing EGM analysis module 90 with digitized EGM signals. Alternatively, analog EGM signals may be provided to EGM analysis module 90 and digitized as needed for performing EGM signal analysis.

EGM analysis module 90 may perform EGM signal analysis for use in determining capture thresholds and whether capture has occurred. For example, a capture threshold module 92 may be included to detect capture and/or loss of capture LOC when signal generator 84 delivers a pacing pulse. Capture threshold information may be used with other EGM analysis information for adjusting pacing therapy. EGM morphology analysis module 94 may be used for detecting fiducial points of near field EGM signals obtained from the RV sensing electrodes for measuring RV activation times relative to LV pacing pulses also for determining capture and/or loss of capture LOC when signal generator 84 delivers a pacing pulse, as described below.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event, e.g., in another chamber.

The sensing device o FIG. 5 includes triggering device 18 for emitting the trigger signal to LV pacing device 12, as described above, which may be included within circuitry located within the housing 160 of the device 14, for example, or may be position along lead 118 or 122. As described above, the trigger signal may be an optical, acoustic or RF signal.

Figure 6:
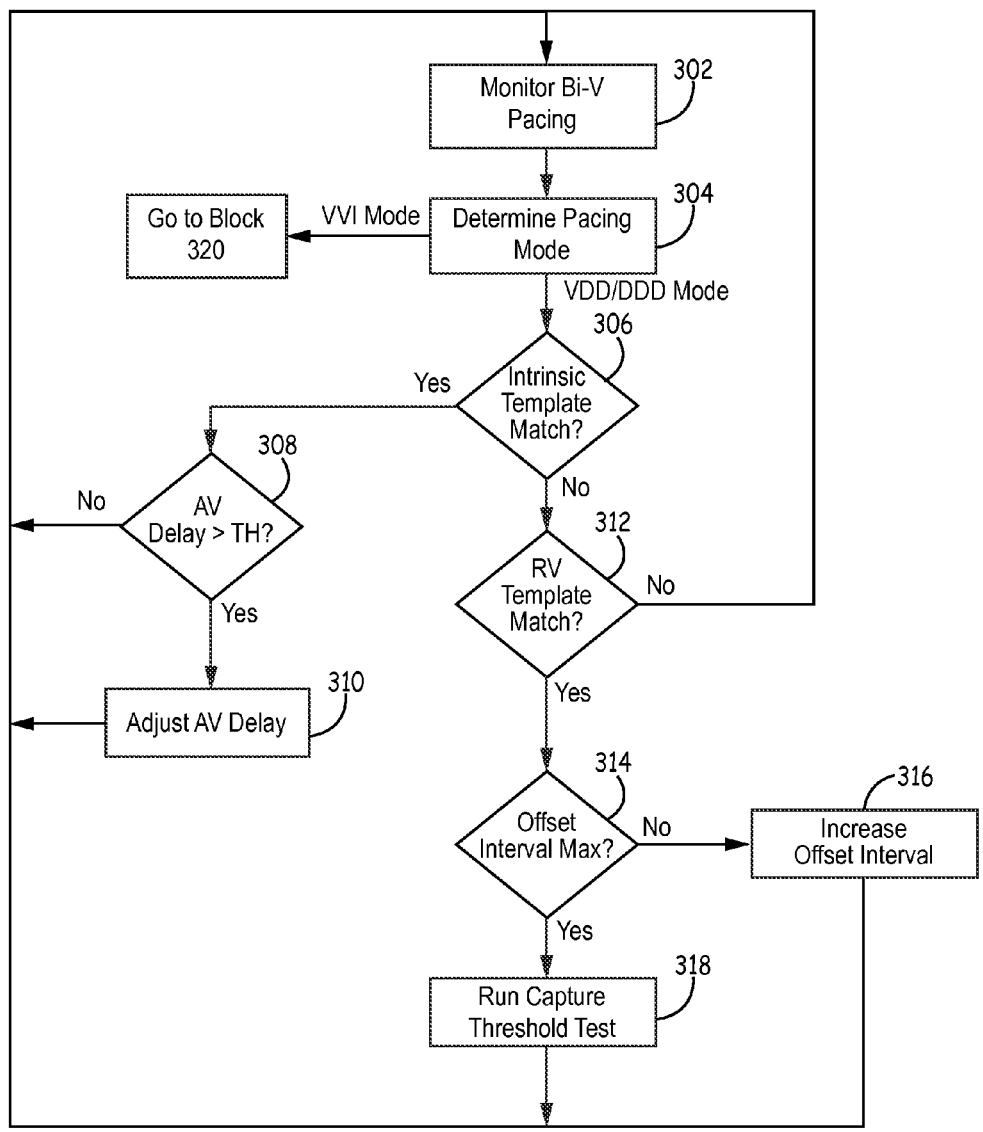
FIG. 6 is a flowchart of a method of delivering bi-ventricular pacing in a medical device system, according to an embodiment of the present disclosure.

FIG. 6 is a flowchart of a method of delivering bi-ventricular pacing in a medical device system, according to an embodiment of the present disclosure. During the delivery of bi-ventricular pacing, the sensing device 14 monitors the delivered bi-ventricular pacing therapy, Block 302. Depending on the cardiac signal being received, the sensing device 14 may operate in either a VDD or a DDD mode, where pacing occurs either only in the ventricle (VDD mode) or in both the ventricle and the atrium (DDD mode) and the sensed subcutaneous cardiac signal is associated with both an atrial and a ventricular signal, or in a VVI mode, where pacing occurs in the ventricle, and the sensed subcutaneous cardiac signal is associated with only a ventricular signal, such as when atrial fibrillation is occurring and therefore the P-wave portion of the subcutaneous cardiac signal is no longer sensed by the sensing device 14 or ventricular pacing is no longer timed off of sensing of P-waves due to a fast atrial rate during atrial arrhythmias. When in either of the VDD mode and the DDD mode, where both a P-wave and an R-wave are included in the sensed subcutaneous cardiac signal, the sensing device 14 times the delivery of the pacing therapy based on the sensed P-wave, so that pacing therapy is delivered by the therapy delivery device 12 each time a P-wave is sensed by the sensing device 14. When in the VVI mode, the sensing device drives the delivery of the pacing therapy based on a predetermined pacing rate, defined by a pacing cycle length, such as 800 ms for example, so that pacing is delivered by the therapy delivery device 14 every 800 ms. In this way, when in either of the VDD mode or the DDD mode, the sensing device 14 senses a subcutaneous cardiac signal associated with both the atrium and the ventricle, and when in the VVI mode, the sensing device 14 senses a subcutaneous cardiac signal associated only with the ventricle.

If, while in either the VDD mode or the DDD mode, the subcutaneous cardiac signal sensed by sensing device 14 no longer includes a discernable P-wave portion of the signal, such as during an episode of atrial fibrillation or rapid atrial activity, the sensing device 14 switches from the VDD mode or the DDD mode to the VVI mode, so that delivery of the pacing is driven by the predetermined pacing rate rather than a sensed P-wave. In the same way, if, while in the VVI mode, the cardiac signal sensed by the sensing device 14 includes a discernable P-wave portion of the signal along with the R-wave portion, the sensing device 14 switches from the VVI mode to either the VDD mode or the DDD mode, so that delivery of the pacing therapy is timed based on the sensed P-wave.

Therefore, the sensing device 14 determines, based on whether the subsequent sensed beat includes both a P-wave and an R-wave portion, which pacing mode is to be utilized, Block 304, and adjusts particular parameters of the pacing therapy. For example, according to one embodiment, if the subsequently sensed signal includes both a P-wave portion and an R-wave portion, and therefore a VDD pacing mode or a DDD mode (depending on whether the RA device 13 includes pacing abilities) is determined in Block 304, the sensing device 14 compares the currently sensed cardiac signal to an intrinsic template associated with the morphology of an intrinsic beat, and determines whether the current beat matches the intrinsic template, Block 306. The determination of whether there is a template match may be made, for example, by calculating a correlation coefficient based on a point-by-point comparison of the sampled signal and the stored baseline intrinsic template, and comparing the correlation coefficient to a predetermined correlation coefficient threshold. Calculation of a correlation coefficient may be performed, for example, as generally described in U.S. Pat. No. 5,193,550 issued to Duffin, incorporated herein by reference in its entirety. According to another embodiment, the determination of whether there is a template match may be made, for example, by determining whether a peak-to-peak amplitude of the template and the current sensed beat is less than a predetermined amplitude. Yet another embodiment may involve comparison of wavelet-transformations of a sampled signal and the stored template and computing a match-score as an index of similarity between ordered wavelet coefficients of the signal and the template, as generally described in U.S. Pat. No. 6,393,316 issued to Gillberg, incorporated herein by reference in its entirety.

If the current beat matches the intrinsic template, Yes in Block 306, the sensing device 14 determines whether the current set atrioventricular delay used during delivery of the pacing therapy is greater than a predetermined atrioventricular delay threshold, Block 308. According to the present disclosure, the atrioventricular delay threshold is within a programmable range, such as from 60-100 ms for example. In one embodiment, threshold for the sensed atrioventricular delay would be 80 ms and the threshold for the paced atrioventricular delay would be 90 ms. If the current set atrioventricular delay used during delivery of the pacing therapy is greater than the predetermined atrioventricular delay threshold, Yes in Block 308, the sensing device 14 adjusts the atrioventricular delay by a predetermined adjustment value. For example, according to one embodiment, the sensing device 14 adjusts the atrioventricular delay, Block 310, by decreasing the atrioventricular delay by a predetermined amount, such as 10 milliseconds, for example. Once the atrioventricular delay is adjusted, Block 310, or if the current set atrioventricular delay used during delivery of the pacing therapy is not determined to be greater than the predetermined atrioventricular delay threshold, No in Block 308, the sensing device 14 continues monitoring the delivered bi-ventricular pacing, Block 302, and the process is repeated for the next cardiac signal sensed during the delivered bi-ventricular pacing.

If the current beat is determined not to match the intrinsic template, No in Block 306, the sensing device 14 compares the currently sensed cardiac signal to an RV-only pacing template associated with the morphology of RV-only pacing, and determines whether the current beat matches the RV-only pacing template, Block 312. If the current beat is determined not to match the RV-only pacing template, No in Block 312, the sensing device 14 continues monitoring the delivered bi-ventricular pacing, Block 302, and the process is repeated for the next cardiac signal sensed during the delivered bi-ventricular pacing. If the current beat is determined to match the RV-only pacing template, Yes in Block 312, the sensing device 14 determines whether a V-V delay is programmed so that contraction of the left ventricle LV is ahead of contraction of the right ventricle RV (pre-excitation or LV-RV delay) by the maximum programmable LV-RV offset interval, Block 314. A maximum level of this LV-RV offset interval is the maximum programmable V-V pre-excitation beyond which the second ventricle will no longer be captured by the bi-ventricular pacing, and therefore effective bi-ventricular pacing will no longer be taking place. According to one embodiment, an exemplary value of the maximum level of this LV-RV offset interval may be set as 100 ms for example.

If the LV-RV delay is currently set so that the left ventricle LV leads the right ventricle RV by the predetermined maximum LV-RV offset interval, Yes in Block 314, the sensing device 14 performs a left ventricular capture test, described below, to set new left ventricular pacing outputs, if necessary, so that effective capture during the bi-ventricle can be achieved, Block 318. Upon completion of the capture threshold test, Block 318, the sensing device 14 continues monitoring the delivered bi-ventricular pacing, Block 302, and the process is repeated for the next cardiac signal sensed during the subsequently delivered bi-ventricular pacing.

If the LV-RV delay is not currently set to a predetermined maximum offset level, No in Block 314, the sensing device 14 increases the V-V delay by increasing the left ventricular offset interval, Block 316, by a predetermined delta, such as 20 ms for example. It is understood that if, for example, the predetermined maximum offset level associated with the left ventricular LV pre-excited bi-ventricular pacing is 100 ms, the sensing device 14 takes into account whether the LV-RV offset interval can be increased by the predetermined delta and nevertheless not exceed the maximum offset interval level. For example, if the LV-RV offset interval is currently set at 90 ms, and therefore less than the maximum offset interval level, increasing the pre-excitation by 20 ms would result in the LV-RV offset interval being increased to 110 ms, which is greater than the maximum offset interval level (90 ms+20 ms=110 ms) of 100 ms. Therefore, the sensing device determines in Block 314 that the LV-RV offset interval is currently set to a predetermined maximum offset interval level, Yes in Block 314.

Once the LV-RV offset interval has been increased, Block 316, or if the LV-RV offset interval is determined to be set to the predetermined maximum offset interval level, Yes in Block 314, the sensing device 14 continues monitoring the delivered bi-ventricular pacing, Block 302, and the process is repeated for the next cardiac signal sensed during subsequently delivered biventricular pacing.

Figure 7:
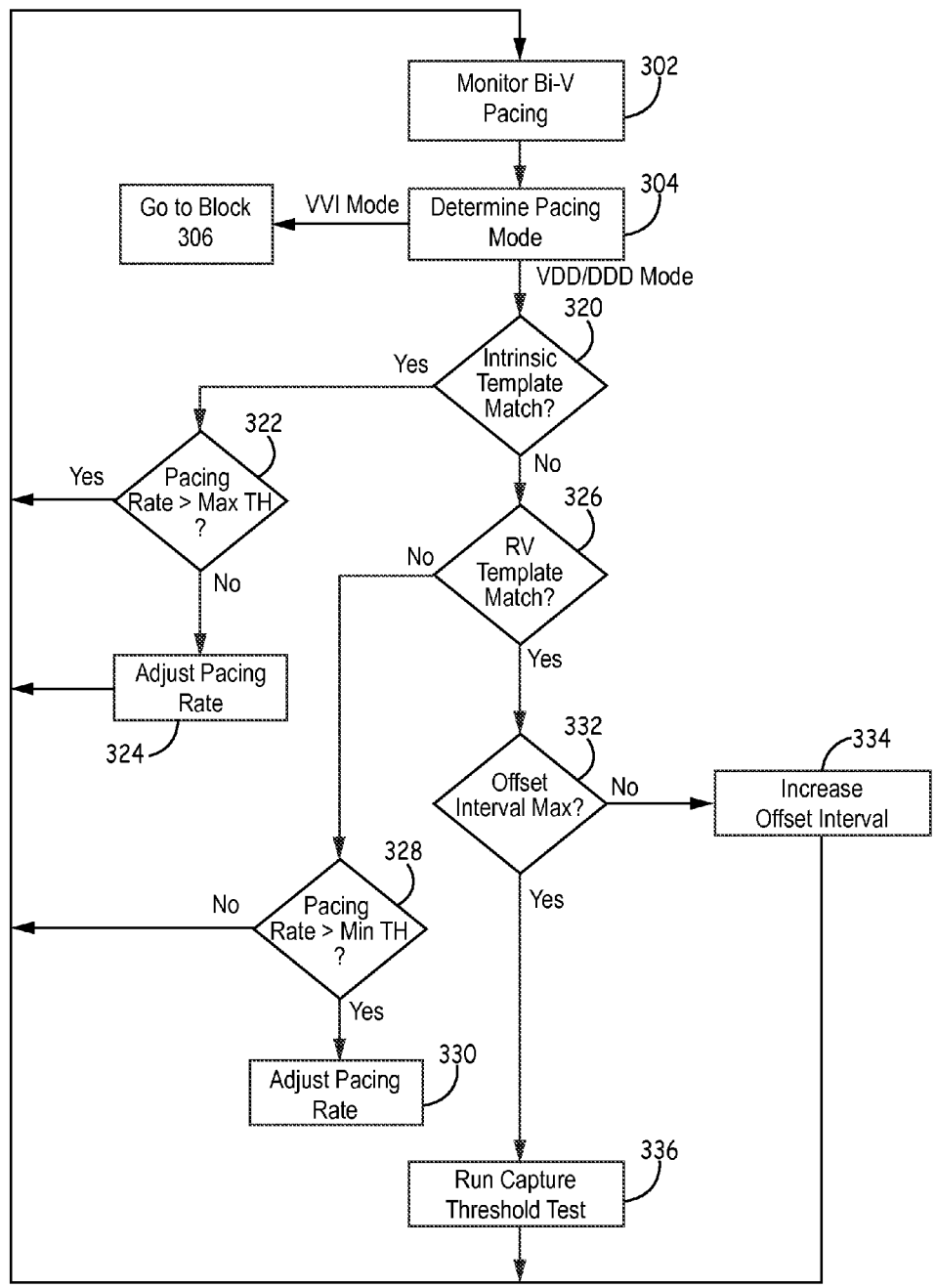
FIG. 7 is a flowchart of a method of delivering bi-ventricular pacing in a medical device system, according to an embodiment of the present disclosure.

FIG. 7 is a flowchart of a method of delivering bi-ventricular pacing in a medical device system, according to an embodiment of the present disclosure. As illustrated in FIG. 7, if the subsequently sensed beat does not include a P-wave portion, such as would occur during an episode of atrial fibrillation, a VVI pacing mode is determined in Block 304. While in the VVI mode, the sensing device 14 compares the currently sensed cardiac signal associated with delivered bi-ventricular pacing therapy to an intrinsic template associated with the morphology of an intrinsic beat, and determines whether the current beat matches the intrinsic template, Block 320, as described above. If the current beat matches the intrinsic template, Yes in Block 320, the sensing device 14 determines whether the current set pacing rate associated with the delivered bi-ventricular pacing therapy is greater than a maximum pacing rate threshold, Block 322. The maximum pacing rate threshold may be set as the maximum programmable pacing rate minus a predetermined delta, such as 2 beats per minute, for example. An exemplary maximum rate may be 100 bpm, 105 bpm, 110 bpm, 115 bpm, 120 bpm, 125 bpm, or 130 bpm, for example.

If the pacing rate associated with the delivered bi-ventricular pacing therapy is determined by the sensing device 14 not to be greater than the maximum pacing rate threshold, No in Block 322, the sensing device 14 adjusts the pacing rate associated with the delivered bi-ventricular pacing therapy, Block 324, such as by increasing the pacing rate by a predetermined amount, such as 2 beats per minute, for example, Block 324, and emits a trigger signal via the trigger signal emitting device 114 instructing the therapy delivery device 12 to adjust the pacing rate of the delivered bi-ventricular pacing therapy to the adjusted rate, during subsequent delivery of the bi-ventricular pacing therapy, Block 302 and the process continues using the adjusted pacing rate. If the pacing rate associated with the delivered ventricular pacing therapy is determined by the sensing device 14 to be greater than the maximum pacing rate threshold, Yes in Block 322, no change is made to the pacing rate and the sensing device 14 continues monitoring the delivered bi-ventricular pacing, Block 302, and the process is repeated for the next sensed cardiac signal.

If the current beat is determined to not match the intrinsic template, No in Block 320, the sensing device 14 compares the currently sensed cardiac signal to an RV-only pacing template associated with the morphology of RV only pacing, and determines whether the current beat matches the RV-only pacing template, Block 326, as described above. If the current beat is determined not to match the RV-only pacing template, No in Block 326, the sensing device 14 determines whether a pacing rate associated with the delivered bi-ventricular pacing therapy is greater than a minimum pacing rate threshold, Block 328. The minimum pacing rate threshold may be set as the minimum programmable pacing rate plus a predetermined delta, such as 2 beats per minute, for example. An exemplary minimum rate may be 40 bpm, 45 bpm, 50 bpm, 55 bpm, or 60 bpm, for example.

If the pacing rate associated with the delivered bi-ventricular pacing therapy is determined by the sensing device 14 to be greater than the minimum pacing rate threshold, Yes in Block 328, the sensing device 14 adjusts the pacing rate by a predetermined amount, Block 330, such as reducing the pacing rate by 2 beats per minute, for example, and the process continues as described above using the adjusted pacing rate during subsequently delivered bi-ventricular pacing therapy. If the pacing rate associated with the delivered ventricular pacing therapy is determined by the sensing device 14 not to be greater than the minimum pacing rate threshold, No in Block 328, no changes are made to the delivered therapy and the sensing device 14 continues monitoring the delivered bi-ventricular pacing, Block 302, and the process is repeated for the next sensed cardiac signal.

If the current beat is determined to match the RV-only pacing template, Yes in Block 326, the sensing device 14 determines whether the LV-RV offset interval is set to a maximum level, Block 332, such as 100 ms for example, as described above. If the LV-RV offset interval is currently set to the predetermined maximum level, Yes in Block 314, the sensing device 14 performs a capture management analysis routine for determining whether or not the pacing output associated with the current bi-ventricular pacing therapy delivered effectively captures the patient's heart, described below in detail. Upon completion of the capture threshold test, Block 336, the sensing device 14 continues monitoring the delivered bi-ventricular pacing, Block 302, and the process is repeated for the next sensed cardiac signal.

Figure 8:
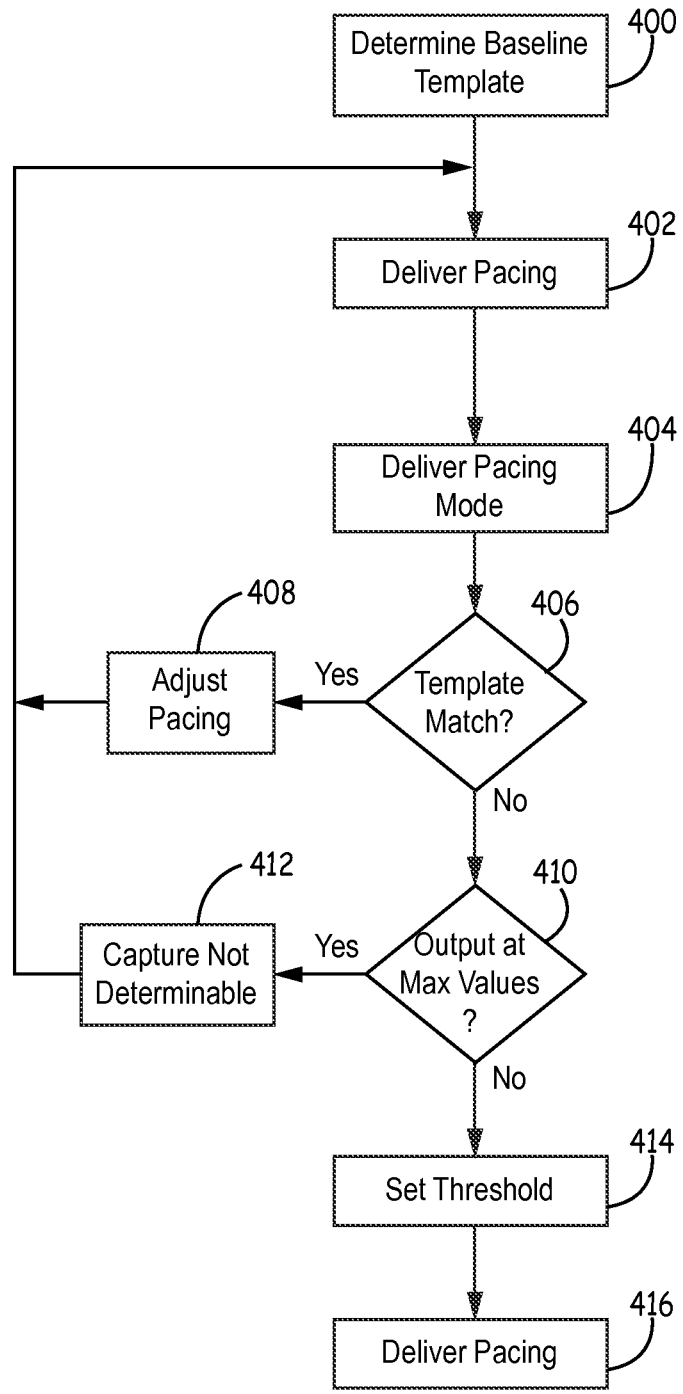
FIG. 8 is a flowchart of a method of determining capture during delivery of bi-ventricular pacing therapy in a medical device system, according to an embodiment of the present disclosure.

FIG. 8 is a flowchart of a method of determining capture during delivery of bi-ventricular pacing therapy in a medical device system, according to an embodiment of the present disclosure. As illustrated in FIG. 8, according to an embodiment of the present disclosure, in order to perform a capture management analysis routine for determining whether or not the pacing output associated with the pacing therapy effectively captures the patient's heart (Blocks 318 and 336), a baseline intrinsic template associated with an intrinsic beat sensed during normal activity of the heart when the sensed beat includes both a P-wave portion and an R-wave portion is determined, Block 400.

Once the baseline intrinsic template is determined, the sensing device 14 emits a trigger signal via the trigger signal emitting device 114, which is then received by the LV pacing device 12 and the RA pacing device 13, and instructs the LV pacing device 12 and the RA pacing device 13 to begin delivering the ventricular pacing therapy, Block 402. The trigger signal emitted by the sensing device 14 initially instructs the LV pacing device 12 and the RA pacing device 13 to deliver the left ventricular pacing therapy using a short atrioventricular delay, such as between 10 ms and 18 ms, and the highest available ventricular pacing output, such as 8 volts, for example. Once the ventricular pacing therapy is delivered by the LV pacing device 12 and the RA pacing device 13, Block 402, the sensing device 14 senses the resulting subcutaneous cardiac signal via far-field sensors 16 and 18, and identifies a subsequent beat within the sensed signal resulting from the delivered ventricular pacing therapy.

The sensing device 14 determines, based on whether the subsequent sensed beat includes both a P-wave and an R-wave portion, which pacing mode is being utilized, Block 404, and therefore which template is to be utilized for the subsequently sensed subcutaneous signal, as described above. For example, according to one embodiment, if the subsequently sensed signal includes both a P-wave portion and an R-wave portion, and therefore a VDD pacing mode is determined in Block 304, the sensing device 14 sets a timing window for the subsequently sensed subcutaneous signal that is to be compared to a timing window of the baseline intrinsic template using a P-wave offset, as described below in FIG. 9A. On the other hand, if the subsequently sensed beat does not include a P-wave portion, and therefore a WI mode is determined in Block 404, the sensing device 14 sets a timing window for the subsequently sensed subcutaneous signal that is to be compared to a timing window of the baseline intrinsic template based on timing of the ventricular pacing event rather than the P-wave, as described below in FIG. 9B.

The sensing device 12 compares the subsequent beat to the chosen stored baseline intrinsic template to determine whether or not the sensed beat resulting from the delivered ventricular pacing therapy matches the template, Block 406, and therefore whether or not the delivered ventricular pacing therapy is effective at capturing the patient's heart. In particular, for example, the sensing device 14 determines whether there is a template match between the subsequently sensed beat resulting from the delivered pacing and the baseline intrinsic template associated with an intrinsic beat. The determination of whether there is a template match may be made, for example, by calculating a correlation coefficient based on a point-by-point comparison of the sampled signal and the stored baseline intrinsic template, and comparing the correlation coefficient to a predetermined correlation coefficient threshold. Calculation of a correlation coefficient may be performed, for example, as generally described in U.S. Pat. No. 5,193,550 issued to Duffin, incorporated herein by reference in its entirety. According to another embodiment, the determination of whether there is a template match may be made, for example, by determining whether a peak-to-peak amplitude of the template and the current sensed beat is less than a predetermined amplitude. Yet another embodiment may involve comparison of wavelet-transformations of sampled signal and the stored template and compute a match-score as an index of similarity between ordered wavelet coefficients of the signal and the template, as generally described in U.S. Pat. No. 6,393,316 issued to Gillberg, incorporated herein by reference in its entirety.

Figure 9A:
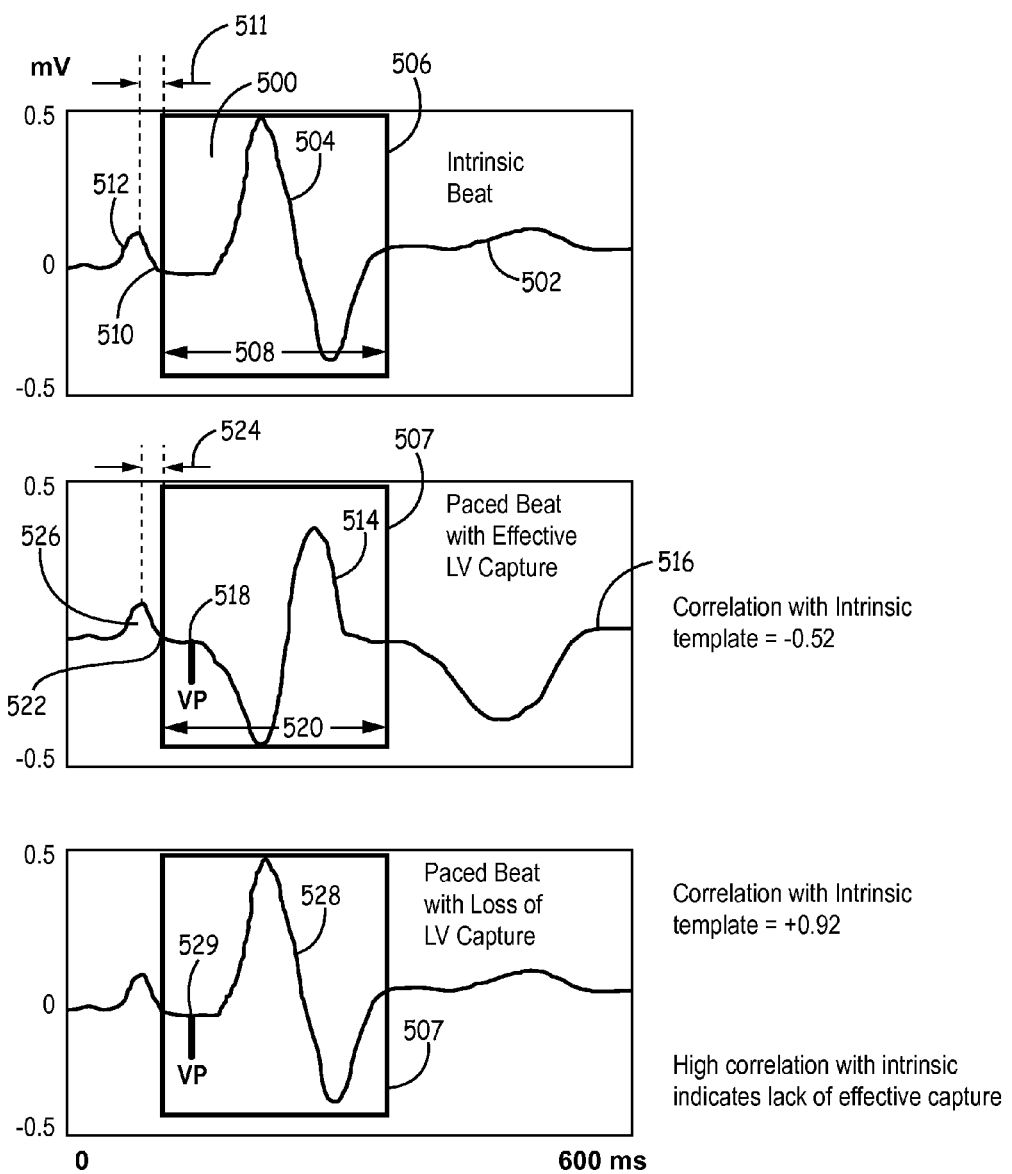
FIG. 9A is a schematic diagram illustrating determining whether a delivered ventricular pacing therapy effectively captures a patient's heart in a medical device system, according to an embodiment of the present disclosure.

FIG. 9A is a schematic diagram illustrating determining whether a delivered ventricular pacing therapy effectively captures a patient's heart in a medical device system, according to an embodiment of the present disclosure. As illustrated in FIG. 9A, in order to determine the baseline intrinsic template 500 associated with a normal intrinsic beat, the sensing device 12 senses a subcutaneous cardiac signal 502 via subcutaneous electrodes 16 and 18 during a period of time that ventricular pacing therapy is not being delivered by the therapy delivery device 12. Once a QRS complex, or R-wave 504 of the sensed cardiac signal 502 is determined to occur, the sensing device 14 determines a timing window 506 having a predetermined width 408, such as 200 ms, for example, and a window starting point 510 located a predetermined P-wave offset 511 distance, such as 40 ms for example, from a corresponding P-wave 512 occurring prior to the sensed R-wave 504 of the QRS complex.

As illustrated in FIG. 9A, when the sensing device 14 senses both a P-wave portion 526 and an R-wave portion 514 in the subcutaneous signal 516 sensed as a result of a ventricular pace 518 being delivered, and therefore determines in Block 304 that the device is in the WD mode, a timing window 507 associated with the R-wave portion 514 is determined and compared to the timing window 506 of the baseline intrinsic template 500, and a resulting correlation coefficient is determined based on the comparison. In particular, as illustrated in FIG. 9A, according to one embodiment, during the determination of the timing window 507 for the resulting paced beat 514, the sensing device 14 determines the timing window 507 as having a window starting point 522 located the predetermined P-wave offset distance 524 from the P-wave 526 and extending the predetermined width 420, i.e., 200 ms, from the starting point 522.

According to the present disclosure, a subsequently sensed beat associated with a sensed subcutaneous cardiac signal and determined by the sensing device 14 to have a high correlation with the baseline intrinsic template indicates that the ventricular pacing therapy delivered by the therapy delivery device 12 does not effectively capture the heart. On the other hand, a determination that the sensed beat does not have a high correlation with the baseline intrinsic template indicates that the delivered ventricular pacing therapy does effectively capture the heart. According to one embodiment, a subsequently sensed beat is determined to be correlated with the baseline intrinsic template 400 if the correlation of the beat to the template is greater than a predetermined correlation threshold, such as 0.75 for example. A correlation coefficient greater than a certain threshold value is an indicator of match between sampled signal and intrinsic template. Exemplary values of threshold may be 0.6, 0.65, 0.75, 0.8. 0.85, 0.9, 0.95, for example.

Therefore, as illustrated in the exemplary schematic diagram of FIG. 9A, when a subsequently sensed beat or R-wave, such as R-wave 514 in FIG. 9A, sensed by the sensing device 14 during delivery of the ventricular pacing therapy Vp 518 by the therapy delivery device 12 is determined to be less than the correlation threshold and therefore not to be highly correlated with the baseline intrinsic template 500, i.e., the correlation of the beat 514 is determined to be −0.52, the paced beat 514 associated with the delivered ventricular pacing therapy indicates effective capture of the heart. On the other hand, when a subsequently sensed beat or R-wave, such as R-wave 528 in FIG. 9A for example, sensed during delivery of the ventricular pacing therapy Vp 529 is determined not to be less than the correlation threshold and therefore highly correlated with the baseline intrinsic template 500, i.e., the correlation of the beat 528 is determined to be +0.92, the paced beat 528 associated with the delivered ventricular pacing therapy indicates ineffective capture of the heart, or loss of capture of the heart.

Figure 9B:
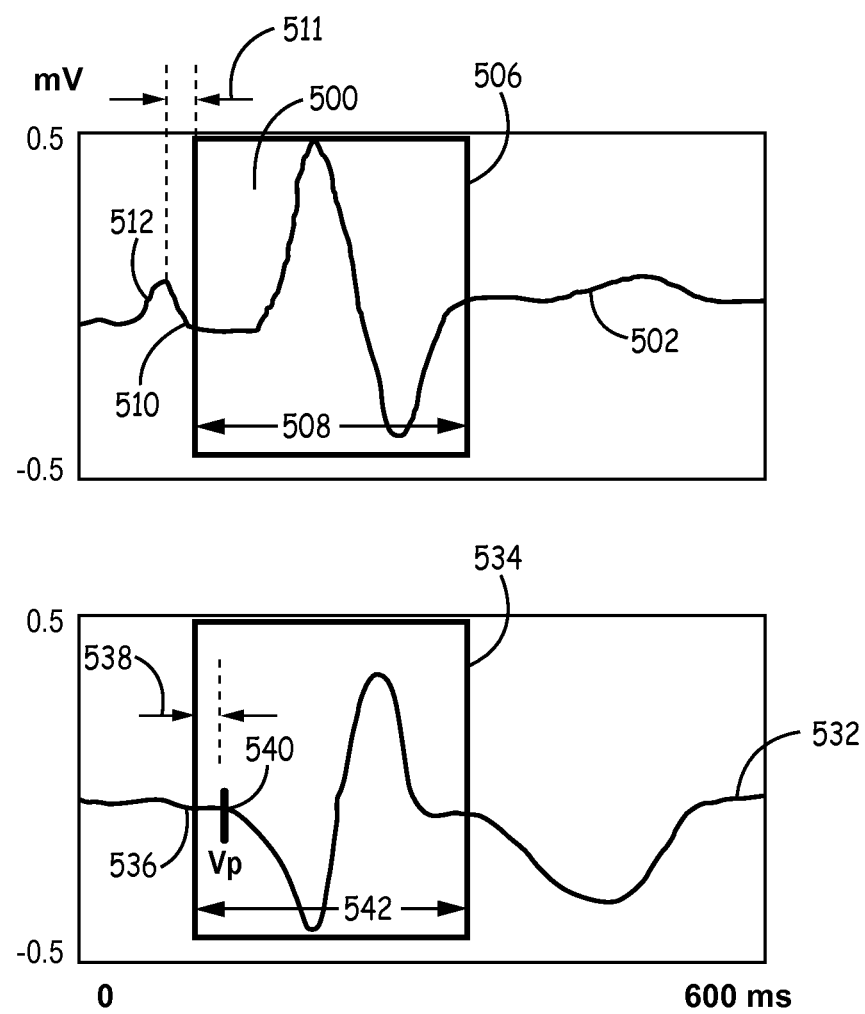
FIG. 9B is a schematic diagram illustrating determining whether a delivered bi-ventricular pacing therapy effectively captures a patient's heart in a medical device system, according to an embodiment of the present disclosure.

FIG. 9B is a schematic diagram illustrating determining whether a delivered ventricular pacing therapy effectively captures a patient's heart in a medical device system, according to an embodiment of the present disclosure. As illustrated in FIG. 9B, when the sensing device 14 does not sense a P-wave portion and senses only an R-wave portion 530 in the subcutaneous signal 532 sensed as a result of a ventricular pace 534 being delivered, and therefore determines in Block 304 that the device is in the VVI mode, a timing window 534 associated with the R-wave portion 530 is determined as having a window starting point 536 located a predetermined V-pace offset distance 538, such as 40 ms for example, from a delivered ventricular pace 540 and extending the predetermined width 542, i.e., 200 ms, from the starting point 536. The timing window 534 is then compared to the timing window 506 of the baseline intrinsic template 500, after aligning the sampled signal with the intrinsic baseline template 500 based on the matching of fiducial points defined by the first change of sign of the slope with amplitude above a certain level (e.g. greater than 0.5 mV), the most dominant peak or valley, or the slope crossing a certain threshold, for example, and a resulting correlation coefficient is determined based on the comparison.

Returning to FIG. 8, therefore, if the ventricular pacing therapy is determined to match the baseline intrinsic template, Yes in Block 406, indicating that a lack of effective pacing or loss of capture is determined to occur, the sensing device 14 adjusts the pacing output, Block 408, and sends the trigger signal to the therapy delivery device 12 instructing the therapy delivery device 12 to deliver the ventricular pacing therapy using the adjusted pacing output. The therapy delivery device 12 receives the trigger signal and delivers the ventricular pacing therapy using the adjusted pacing output, Block 402, and the sensing device 14 then repeats the comparison of a resulting subsequent beat, sensed by the sensing device 14 during delivery of the ventricular pacing therapy at the adjusted pacing output by the therapy delivery device 12, to the baseline intrinsic template, Block 402. According to one embodiment, during the adjusting of the pacing output in Block 408, the sensing device 14 may decrement the pacing output by a predetermined amount, such as 0.5 volts for example.

If the beat is determined not to match the baseline intrinsic template, No in Block 406, and therefore effective ventricular pacing therapy or capture is determined to occur, the sensing device 14 determines whether the current pacing output is set as the highest rate, Block 410. If the current pacing output is set at the highest rate, Yes in Block 410, the sensing device 14 determines that left ventricular capture is not currently determinable, Block 342, and the therapy delivery device 12 continues delivering the ventricular pacing therapy, Block 402. If the current pacing output is not set at the highest rate, No in Block 410, the sensing device 14 sets the pacing output threshold equal to the current pacing output plus a predetermined delta, Block 414. Exemplary predetermined deltas may be 0.5V, 1. V, 1.5 V or 2.0V above the threshold pacing output voltage.

Once the pacing output threshold is determined in Block 414, the sensing device 14 emits a trigger signal that is then received by the therapy delivery device and instructs the therapy delivery device to deliver ventricular pacing therapy using the set pacing output threshold, Block 414, and an initial or predetermined pacing rate. The pacing rate may be programmable, and exemplary initial pacing rates may be 40 bpm, 45 bpm, 50 bpm, 55 bpm, 60 bpm, 65 bpm, 70 bpm, 75 bpm, 80 bpm, 90 bpm, 95 bpm, 100 bpm, 105 bpm, 110 bpm.

The techniques described in this disclosure, including those attributed to the IMD, the programmer, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A medical device system for delivering a bi-ventricular pacing therapy, comprising:
   a leadless pacing device capable of being positioned within a left ventricle of a patient's heart and comprising electrodes to deliver the bi-ventricular pacing therapy;
   an implantable medical device comprising a plurality of electrodes and capable of being positioned within a right ventricle of the heart to deliver the bi-ventricular pacing therapy and to sense a cardiac signal;

an emitting device to emit a trigger signal to control delivery of the bi-ventricular pacing therapy; and a processor configured to compare the sensed cardiac signal associated with the delivered bi-ventricular pacing to at least one of an intrinsic beat template and an RV template associated with a morphology of RV-only pacing therapy, determine whether an offset interval associated with the bi-ventricular pacing therapy is set to a maximum offset interval level in response to the comparing, adjust the offset interval in response to the offset interval not being set to the maximum offset interval level, and generate the trigger signal to be emitted by the emitting device to subsequently deliver the bi-ventricular pacing therapy having the adjusted offset interval.

2. The medical device system of claim 1, wherein the processor is configured to determine whether the offset interval associated with the bi-ventricular pacing therapy is set to the maximum offset interval level in response to both the cardiac signal not matching the intrinsic beat template and the cardiac signal matching the RV template.

3. The medical device system of claim 1, wherein the processor is configured to determine, in response to the cardiac signal matching the intrinsic beat template, whether an atrioventricular delay associated with the delivered bi-ventricular pacing therapy is greater than a delay threshold, and adjust the atrioventricular delay in response to the atrioventricular delay being greater than the delay threshold.

4. The medical device system of claim 1, wherein the processor is configured to determine, in response to both the sensed cardiac signal not matching the intrinsic beat template and the cardiac signal not matching the RV template, whether a pacing rate associated with the delivered bi-ventricular pacing therapy is greater than a minimum pacing rate threshold, and adjust the pacing rate in response to the pacing rate associated with the delivered bi-ventricular pacing therapy being greater than the minimum pacing rate threshold.

5. The medical device system of claim 1, wherein the processor is configured to determine, in response to the cardiac signal matching the intrinsic beat template, whether a pacing rate associated with the delivered bi-ventricular pacing therapy is greater than a maximum pacing rate threshold, and adjust the pacing rate in response to the pacing rate associated with the delivered bi-ventricular pacing therapy being greater than the maximum pacing rate threshold.

6. The medical device system of claim 1, wherein the processor is configured to determine whether the medical device system is in one of a VDD/DDD pacing mode and a VVI pacing mode, if in a VDD/DDD pacing mode, determine, in response to the cardiac signal matching the intrinsic beat template, whether an atrioventricular delay associated with the delivered bi-ventricular pacing therapy is greater than a delay threshold, and adjust the atrioventricular delay in response to the atrioventricular delay being greater than the delay threshold, and if in a VVI pacing mode, and if in the VVI pacing mode, determine, in response to both the sensed cardiac signal not matching the intrinsic beat template and the cardiac signal not matching the RV template, whether a pacing rate associated with the delivered bi-ventricular pacing therapy is greater than a minimum pacing rate threshold, and adjust the pacing rate in response to the pacing rate associated with the delivered bi-ventricular pacing therapy being greater than the minimum pacing rate threshold.

7. The medical device system of claim 6, wherein the processor is configured to determine, if in the VVI pacing mode, and in response to the cardiac signal matching the intrinsic beat template, whether a pacing rate associated with the delivered bi-ventricular pacing therapy is greater than a maximum pacing rate threshold, and adjust the pacing rate in response to the pacing rate associated with the delivered bi-ventricular pacing therapy being greater than the maximum pacing rate threshold.

8. The medical device system of claim 7, wherein the processor is configured to determine whether the offset interval associated with the bi-ventricular pacing therapy is set to a maximum offset interval level in response to both the cardiac signal not matching the intrinsic beat template and the cardiac signal matching the RV template.

9. The medical device system of claim 8, wherein the processor is configured to determine whether to adjust pacing outputs associated with the delivered bi-ventricular pacing therapy in response to the offset interval being set to the maximum offset interval level.

10. A medical device system for delivering a bi-ventricular pacing therapy, comprising:

a leadless pacing device capable of being positioned within a left ventricle of a patient's heart and comprising electrodes to deliver the bi-ventricular pacing therapy;

a leadless pacing device capable of being positioned within a right ventricle of a patient's heart and comprising electrodes to deliver the bi-ventricular pacing therapy;

a subcutaneously implantable device comprising a subcutaneous electrode to sense a cardiac signal;

an emitting device to emit a trigger signal to control delivery of the bi-ventricular pacing therapy; and a processor configured to compare the sensed cardiac signal associated with the delivered bi-ventricular pacing to at least one of an intrinsic beat template and an RV template associated with a morphology of RV-only pacing therapy, determine whether an offset interval associated with the bi-ventricular pacing therapy is set to a maximum offset interval level in response to the comparing, adjust the offset interval in response to the offset interval not being set to the maximum offset interval level, and generate the trigger signal to be emitted by the emitting device to subsequently deliver the bi-ventricular pacing therapy having the adjusted offset interval.

11. The medical device system of claim 10, wherein the processor is configured to determine whether the offset interval associated with the bi-ventricular pacing therapy is set to the maximum offset interval level in response to both the cardiac signal not matching the intrinsic beat template and the cardiac signal matching the RV template.

12. The medical device system of claim 10, wherein the processor is configured to determine, in response to the cardiac signal matching the intrinsic beat template, whether an atrioventricular delay associated with the delivered bi-ventricular pacing therapy is greater than a delay threshold, and adjust the atrioventricular delay in response to the atrioventricular delay being greater than the delay threshold.

13. The medical device system of claim 10, wherein the processor is configured to determine, in response to both the sensed cardiac signal not matching the intrinsic beat template and the cardiac signal not matching the RV template, whether a pacing rate associated with the delivered bi-ventricular pacing therapy is greater than a minimum pacing rate threshold, and adjust the pacing rate in response to the pacing rate associated with the delivered bi-ventricular pacing therapy being greater than the minimum pacing rate threshold.

14. The medical device system of claim 10, wherein the processor is configured to determine, in response to the cardiac signal matching the intrinsic beat template, whether a pacing rate associated with the delivered bi-ventricular pacing therapy is greater than a maximum pacing rate threshold, and adjust the pacing rate in response to the pacing rate associated with the delivered bi-ventricular pacing therapy being greater than the maximum pacing rate threshold.

15. The medical device system of claim 10, wherein the processor is configured to determine whether the medical device system is in one of a VDD/DDD pacing mode and a VVI pacing mode, if in a VDD/DDD pacing mode, determine, in response to the cardiac signal matching the intrinsic beat template, whether an atrioventricular delay associated with the delivered bi-ventricular pacing therapy is greater than a delay threshold, and adjust the atrioventricular delay in response to the atrioventricular delay being greater than the delay threshold, and if in a VVI pacing mode, and if in the VVI pacing mode, determine, in response to both the sensed cardiac signal not matching the intrinsic beat template and the cardiac signal not matching the RV template, whether a pacing rate associated with the delivered bi-ventricular pacing therapy is greater than a minimum pacing rate threshold, and adjust the pacing rate in response to the pacing rate associated with the delivered bi-ventricular pacing therapy being greater than the minimum pacing rate threshold.

16. The medical device system of claim 15, wherein the processor is configured to determine, if in the VVI pacing mode, and in response to the cardiac signal matching the intrinsic beat template, whether a pacing rate associated with the delivered bi-ventricular pacing therapy is greater than a maximum pacing rate threshold, and adjust the pacing rate in response to the pacing rate associated with the delivered bi-ventricular pacing therapy being greater than the maximum pacing rate threshold.

17. The medical device system of claim 16, wherein the processor is configured to determine whether the offset interval associated with the bi-ventricular pacing therapy is set to a maximum offset interval level in response to both the cardiac signal not matching the intrinsic beat template and the cardiac signal matching the RV template.

18. The medical device system of claim 17, wherein the processor is configured to determine whether to adjust pacing outputs associated with the delivered bi-ventricular pacing therapy in response to the offset interval being set to the maximum offset interval level.

19. An implantable medical device for delivering a bi-ventricular pacing therapy, comprising:
a plurality of electrodes to sense a cardiac signal;
an emitting device to emit a trigger signal to control delivery of the bi-ventricular pacing; and
a processor configured to compare the sensed cardiac signal associated with the delivered bi-ventricular pacing to at least one of an intrinsic beat template and an RV template associated with a morphology of RV-only pacing therapy, determine whether an offset interval associated with the bi-ventricular pacing therapy is set to a maximum offset interval level in response to the comparing, adjust the offset interval in response to the offset interval not being set to the maximum offset interval level, and generate the trigger signal to be emitted by the emitting device to subsequently deliver the bi-ventricular pacing therapy having the adjusted offset interval.

20. The medical device system of claim 19, wherein the processor is configured to determine whether the offset interval associated with the bi-ventricular pacing therapy is set to the maximum offset interval level in response to both the cardiac signal not matching the intrinsic beat template and the cardiac signal matching the RV template.

21. The medical device system of claim 19, wherein the processor is configured to determine, in response to the cardiac signal matching the intrinsic beat template, whether an atrioventricular delay associated with the delivered bi-ventricular pacing therapy is greater than a delay threshold, and adjust the atrioventricular delay in response to the atrioventricular delay being greater than the delay threshold.

22. The medical device system of claim 19, wherein the processor is configured to determine, in response to both the sensed cardiac signal not matching the intrinsic beat template and the cardiac signal not matching the RV template, whether a pacing rate associated with the delivered bi-ventricular pacing therapy is greater than a minimum pacing rate threshold, and adjust the pacing rate in response to the pacing rate associated with the delivered bi-ventricular pacing therapy being greater than the minimum pacing rate threshold.

23. The medical device system of claim 19, wherein the processor is configured to determine, in response to the cardiac signal matching the intrinsic beat template, whether a pacing rate associated with the delivered bi-ventricular pacing therapy is greater than a maximum pacing rate threshold, and adjust the pacing rate in response to the pacing rate associated with the delivered bi-ventricular pacing therapy being greater than the maximum pacing rate threshold.

24. The medical device system of claim 19, wherein the processor is configured to determine whether the medical device system is in one of a VDD/DDD pacing mode and a VVI pacing mode, if in a VDD/DDD pacing mode, determine, in response to the cardiac signal matching the intrinsic beat template, whether an atrioventricular delay associated with the delivered bi-ventricular pacing therapy is greater than a delay threshold, and adjust the atrioventricular delay in response to the atrioventricular delay being greater than the delay threshold, and if in a VVI pacing mode, and if in the VVI pacing mode, determine, in response to both the sensed cardiac signal not matching the intrinsic beat template and the cardiac signal not matching the RV template, whether a pacing rate associated with the delivered bi-ventricular pacing therapy is greater than a minimum pacing rate threshold, and adjust the pacing rate in response to the pacing rate associated with the delivered bi-ventricular pacing therapy being greater than the minimum pacing rate threshold.

25. The medical device system of claim 24, wherein the processor is configured to determine, if in the VVI pacing mode, and in response to the cardiac signal matching the intrinsic beat template, whether a pacing rate associated with the delivered bi-ventricular pacing therapy is greater than a maximum pacing rate threshold, and adjust the pacing rate in response to the pacing rate associated with the delivered bi-ventricular pacing therapy being greater than the maximum pacing rate threshold.

26. The medical device system of claim 25, wherein the processor is configured to determine whether the offset interval associated with the bi-ventricular pacing therapy is set to a maximum offset interval level in response to both the cardiac signal not matching the intrinsic beat template and the cardiac signal matching the RV template.

27. The medical device system of claim 26, wherein the processor is configured to determine whether to adjust pacing outputs associated with the delivered bi-ventricular pacing therapy in response to the offset interval being set to the maximum offset interval level.

* * * * *